United States Patent [19]
Yankov et al.

[11] Patent Number: 5,840,748
[45] Date of Patent: Nov. 24, 1998

[54] DIHALOCEPHALOMANNINE AND METHODS OF USE THEREFOR

[75] Inventors: Luben K. Yankov, Edison; Ramesh C. Pandey, Highland Park, both of N.J.

[73] Assignee: Xechem International, Inc., New Brunswick, N.J.

[21] Appl. No.: 571,427

[22] Filed: Dec. 13, 1995

Related U.S. Application Data

[63] Continuation-in-part of Ser. No. 530,846, Oct. 2, 1995, abandoned.

[51] Int. Cl.$^6$ ........................ A61K 31/335; C07D 305/14
[52] U.S. Cl. ........................... 514/449; 549/510; 549/511
[58] Field of Search .................................... 549/510, 511; 514/449

[56] References Cited

U.S. PATENT DOCUMENTS

| | | | |
|---|---|---|---|
| 4,814,470 | 3/1989 | Colin et al. | 514/449 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,202,448 | 4/1993 | Carver et al. | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,248,796 | 9/1993 | Chen et al. | 549/510 |
| 5,250,683 | 10/1993 | Holton et al. | 544/60 |
| 5,250,722 | 10/1993 | Bombardelli et al. | 560/104 |
| 5,254,580 | 10/1993 | Chen et al. | 514/449 |
| 5,254,703 | 10/1993 | Holton | 549/510 |
| 5,272,171 | 12/1993 | Ueda et al. | 514/449 |
| 5,274,124 | 2/1993 | Holton | 549/214 |
| 5,278,324 | 1/1994 | Kingston et al. | 549/510 |
| 5,279,949 | 1/1994 | Nair | 435/123 |
| 5,283,253 | 2/1994 | Holton et al. | 514/444 |
| 5,284,864 | 2/1994 | Holton et al. | 514/449 |
| 5,284,865 | 2/1994 | Holton et al. | 514/449 |
| 5,294,637 | 3/1994 | Chen et al. | 514/449 |
| 5,296,506 | 3/1994 | Kingston et al. | 514/449 |
| 5,300,638 | 4/1994 | Farina et al. | 540/357 |
| 5,310,672 | 5/1994 | Wann et al. | 435/240 |
| 5,319,112 | 6/1994 | Kingston et al. | 549/510 |
| 5,334,732 | 8/1994 | Murray et al. | 549/510 |
| 5,336,684 | 8/1994 | Murray et al. | 514/449 |
| 5,336,785 | 8/1994 | Holton | 549/214 |
| 5,338,872 | 8/1994 | Holton et al. | 549/510 |
| 5,412,092 | 5/1995 | Rey et al. | 540/200 |
| 5,470,766 | 11/1995 | Kingston et al. | 544/376 |
| 5,473,055 | 12/1995 | Mongelli et al. | 530/329 |
| 5,475,011 | 12/1995 | Ojima et al. | 514/320 |
| 5,475,120 | 12/1995 | Rao | 549/510 |

OTHER PUBLICATIONS

"Cephalomannine; a New Antitumor Alkaloid from *Cephalotaxus mannii*" by Powell et al., J.C.S. Chem. Comm., pp. 102–105 (1979).

"Biologically Active Taxol Anolgues With Depleted A–Ring Side Chain Substituents and Variable C–2' Configurations" by Swindell et al., J.Med.Chem 34 (37:1176–1184 (1991)).

*Primary Examiner*—Ba K. Trinh
*Attorney, Agent, or Firm*—Duane, Morris & Heckscher LLP

[57] ABSTRACT

Provided are antineoplastic derivatives by a process of selective halogenation of side chains of unsaturated taxanes; more particularly, the process involves the use of halogens, particularly bromine, which is easily added to the side chain double bond of cephalomannine, leaving paclitaxel unchanged, and wherein diastereomeric mixtures of 2", 3"-dibromocephalomannine display high activity against: Leukemia cell line HL-60 (TB); Non-Small Cell Lung Cancer line NCI-H522; Colon Cancer cell lines COLO 205 and HT 29; CNS Cancer cell lines SF-539 and SNB-75; Ovarian Cancer Cell line OVCAR-3; Renal Cancer cell line RXF-393; and Breast Cancer cell lines MCF7, MDA-MB-231/ATCC, HS 578T, MDA-MB-435 and MDA-N.

4 Claims, 45 Drawing Sheets

PACLITAXEL

CEPHALOMANNINE

2″,3″- DIBROMO - CEPHALOMANNINE

| FIG.15A | FIG.15B |
|---|---|
| FIG.15C | FIG.15D |
| FIG.15E | FIG.15F |

FIG. 15A

"ANOLOG"

| | Time | | | Mean Optical Densities | | | | |
|---|---|---|---|---|---|---|---|---|
| | | | | | Log10 Concentration | | | |
| Panel/Cell Line | Zero | Ctrl | -8.0 | -7.0 | -6.0 | -5.0 | -4.0 | |
| Leukemia | | | | | | | | |
| CCRF-CEM | 0.260 | 0.852 | 0.359 | 0.345 | 0.347 | 0.294 | 0.375 | |
| HL-60(TB) | 0.433 | 1.471 | 0.361 | 0.314 | 0.333 | 0.269 | 0.283 | |
| MOLT-4 | 0.343 | 1.327 | 0.676 | 0.584 | 0.501 | 0.417 | 0.283 | |
| RPMI-8226 | 0.786 | 1.748 | 0.924 | 09.11 | 0.881 | 0.798 | 0.764 | |
| SR | 0.331 | 1.056 | 0.354 | 0.325 | 0.310 | 0.270 | 0.348 | |
| Non-Small Cell Lung Cancer | | | | | | | | |
| A549/ATCC | 0.343 | 1.981 | 1.058 | 0.799 | 0.738 | 0.754 | 0.199 | |
| EKVX | 0.398 | 1.133 | 0.977 | 0.897 | 0.771 | 0.706 | 0.252 | |
| HOP-62 | 0.611 | 1.628 | 1.222 | 0.765 | 0.723 | 0.706 | 0.025 | |
| HOP-92 | 0.747 | 1.111 | 0.950 | 0.912 | 0.925 | 0.819 | 0.071 | |
| NCI-H226 | 0.543 | 1.155 | 0.795 | 0.685 | 0.637 | 0.657 | 0.009 | |
| NCI-H23 | 0.389 | 1.456 | 0.528 | 0.374 | 0.388 | 0.481 | 0.083 | |
| NCI-H322M | 0.592 | 1.583 | 1.060 | 0.826 | 0.816 | 0.819 | 0.016 | |
| NCI-H460 | 0.159 | 1.646 | 0.385 | 0.227 | 0.214 | 0.207 | 0.024 | |
| NCI-H522 | 0.462 | 0.939 | 0.396 | 0.238 | 0.155 | 0.191 | | |
| Colon Cancer | | | | | | | | |
| COLO 205 | 0.222 | 1.276 | 0.149 | 0.104 | 0.097 | 0.125 | -0.007 | |
| HCC-2998 | 0.372 | 1.602 | 0.799 | 0.550 | 0.477 | 0.483 | 0.111 | |
| HCT-116 | 0.141 | 1.730 | 0.434 | 0.305 | 0.282 | 0.335 | 0.003 | |
| HT29 | 0.090 | 0.926 | 0.109 | 0.096 | 0.054 | 0.062 | 0.001 | |
| KM12 | 0.230 | 1.298 | 0.371 | 0.317 | 0.310 | 0.314 | 0.051 | |
| SW-620 | 0.139 | 1.259 | 0.456 | 0.475 | 0.445 | 0.436 | 0.003 | |

FIG. 15B

"ANOLOG"

| Log10 Concentration | | | | | | | |
|---|---|---|---|---|---|---|---|
| Percent Growth | | | | | GI50 | TGI | LC50 |
| -8.0 | -7.0 | -6.0 | -5.0 | -4.0 | | | |
| 17 | 14 | 15 | 6 | 19 | <1.00E-08 | >1.00E-04 | >1.00E-04 |
| -17 | -28 | -23 | -36 | -35 | <1.00E-08 | <1.00E-08 | >1.00E-04 |
| 34 | 24 | 16 | 8 | -17 | <1.00E-08 | 2.00E-05 | >1.00E-04 |
| 14 | 13 | 10 | 1 | -3 | <1.00E-08 | 1.97E-05 | >1.00E-04 |
| 3 | -2 | -6 | -18 | 2 | <1.00E-08 | . | >1.00E-04 |
| 44 | 28 | 24 | 25 | -42 | <1.00E-08 | 2.37E-05 | >1.00E-04 |
| 79 | 68 | 51 | 42 | -37 | 1.18E-06 | 3.41E-05 | >1.00E-04 |
| 60 | 15 | 11 | 9 | -100 | 1.67E-08 | 1.22E-05 | 3.49E-05 |
| 56 | 45 | 49 | 20 | -97 | 3.60E-08 | 1.48E-05 | 3.97E-05 |
| 41 | 23 | 15 | 19 | -87 | <1.00E-08 | 1.50E-05 | 4.47E-05 |
| 13 | -4 | 0 | 9 | -98 | <1.00E-08 | . | 3.57E-05 |
| 47 | 24 | 23 | 23 | -86 | <1.00E-08 | 1.62E-05 | 4.68E-05 |
| 15 | 5 | 4 | 3 | -90 | <1.00E-08 | 1.08E-05 | 3.71E-05 |
| -14 | -48 | -66 | -59 | -95 | <1.00E-08 | <1.00E-08 | 1.21E-07 |
| -33 | -53 | -56 | -44 | -100 | <1.00E-08 | <1.00E-08 | . |
| 35 | 14 | 8 | 9 | -70 | 1.00E-08 | 1.30E-05 | 5.55E-05 |
| 13 | 10 | 9 | 12 | -98 | <1.00E-08 | 1.29E-05 | 3.67E-05 |
| 2 | 1 | -40 | -31 | -99 | <1.00E-08 | 1.04E-07 | 1.90E-05 |
| 13 | 8 | 7 | 8 | -76 | <1.00E-08 | 1.23E-05 | 4.73E-05 |
| 28 | 30 | 27 | 27 | -98 | <1.00E-08 | 1.64E-05 | 4.13E-05 |

| | | | | | | | |
|---|---|---|---|---|---|---|---|
| 45 | 32 | 24 | 12 | -83 | <1.00E-08 | 1.35E-05 | 4.52E-05 |
| 66 | 32 | 10 | 10 | -91 | 2.94E-08 | 1.25E-05 | 3.92E-05 |
| 13 | -12 | -36 | -11 | -83 | <1.00E-08 | 3.34E-08 | 3.46E-05 |
| 62 | 40 | 29 | 33 | -33 | 3.49E-08 | 3.18E-05 | >1.00E-04 |
| 36 | -15 | -34 | 0 | -49 | <1.00E-08 | 5.04E-08 | <1.00E-04 |
| 25 | 18 | 14 | 14 | -95 | <1.00E-08 | 1.34E-05 | 3.86E-05 |
| 42 | 30 | 26 | -20 | -95 | <1.00E-08 | 3.86E-06 | 2.53E-05 |
| 46 | 38 | 17 | 36 | -100 | <1.00E-08 | 1.85E-05 | 4.30E-05 |
| 49 | 11 | -47 | 1 | -90 | <1.00E-08 | . | 3.64E-05 |
| 17 | -11 | -14 | 16 | -94 | <1.00E-08 | . | 3.98E-05 |
| 46 | 42 | 48 | 45 | -92 | <1.00E-08 | 2.13E-05 | 4.96E-05 |
| 23 | 15 | 15 | 22 | -79 | <1.00E-08 | 1.64E-05 | 5.15E-05 |
| 42 | 35 | 36 | 41 | -97 | <1.00E-08 | 1.99E-05 | 4.58E-05 |
| 38 | 24 | 15 | 22 | -97 | <1.00E-08 | 1.52E-05 | 4.00E-05 |
| 38 | 30 | 25 | 24 | -80 | <1.00E-08 | 1.70E-05 | 5.16E-05 |
| 4 | -9 | -23 | -9 | -99 | <1.00E-08 | 1.99E-08 | 2.83E-05 |
| 61 | 57 | 52 | 35 | -96 | 1.36E-06 | 1.86E-05 | 4.48E-05 |
| 21 | 15 | 8 | 11 | -93 | <1.00E-08 | 1.28E-05 | 3.86E-05 |
| 28 | 15 | 10 | 11 | -44 | <1.00E-08 | 1.59E-05 | <1.00E-04 |
| 35 | 17 | 5 | 6 | -65 | <1.00E-08 | 1.20E-05 | 6.13E-05 |

*FIG. 15D*

| | | | | | | |
|---|---|---|---|---|---|---|
| Renal Cancer | | | | | | |
| 786-0 | 0.171 | 0.668 | 0.492 | 0.359 | 0.242 | 0.242 | 0.019 |
| A498 | 0.775 | 1.523 | 1.295 | 1.105 | 0.982 | 1.147 | 0.183 |
| ACHN | 0.444 | 1.624 | 1.442 | 1.170 | 0.921 | 0.905 | 0.010 |
| CAKI-1 | 0.379 | 1.003 | 0.969 | 0.823 | 0.605 | 0.385 | 0.007 |
| RXF-393 | 0.462 | 1.023 | 0.656 | 0.499 | 0.359 | 0.428 | 0.038 |
| SN12C | 0.374 | 1.666 | 0.781 | 0.676 | 0.645 | 0.612 | 0.006 |
| TK-10 | 0.667 | 1.278 | 1.243 | 1.071 | 0.902 | 0.837 | 0.366 |
| UO-31 | 0.414 | 1.102 | 1.104 | 1.014 | 0.708 | 0.601 | 0.002 |
| Prostate Cancer | | | | | | |
| PC-3 | 0.440 | 1.737 | 0.824 | 0.644 | 0.584 | 0.606 | 0.056 |
| DU-145 | 0.312 | 1.646 | 0.606 | 0.424 | 0.295 | 0.350 | 0.079 |
| Breast Cancer | | | | | | |
| MCF7 | 0.186 | 0.544 | 0.133 | 0.155 | 0.141 | 0.158 | 0.003 |
| MCF7/ADR-RES | 0.455 | 1.201 | 1.275 | 1.171 | 1.067 | 0.643 | 0.107 |
| MDA-MB-231/ATCC | 0.265 | 0.614 | 0.421 | 0.292 | 0.255 | 0.244 | 0.007 |
| HS 578T | 0.636 | 1.176 | 0.678 | 0.559 | 0.500 | 0.512 | 0.450 |
| MDA-MB-435 | 0.165 | 1.185 | 0.078 | 0.053 | 0.079 | 0.143 | 0.126 |
| MDA-N | 0.229 | 1.466 | 0.059 | 0.053 | 0.035 | 0.088 | 0.002 |
| BT-549 | 0.462 | 1.153 | 0.789 | 0.708 | 0.506 | 1.564 | -0.002 |
| T-47D | 0.439 | 1.300 | 0.739 | 0.671 | 0.653 | 0.603 | 0.011 |

FIG. 15E

| | | | | | | | |
|---|---|---|---|---|---|---|---|
| 65 | 38 | 14 | 14 | -89 | 3.53E-08 | 1.36E-05 | 4.20E-05 |
| 70 | 44 | 28 | 50 | -76 | 5.88E-08 | 2.48E-05 | 6.18E-05 |
| 85 | 62 | 40 | 39 | -98 | 3.53E-07 | 1.93E-05 | 4.47E-05 |
| 95 | 71 | 36 | 1 | -98 | 4.04E-07 | 1.02E-05 | 3.27E-05 |
| 35 | 7 | -22 | -7 | -92 | <1.00E-08 | 1.69E-07 | 3.20E-05 |
| 31 | 23 | 21 | 18 | -99 | <1.00E-08 | 1.44E-05 | 3.84E-05 |
| 94 | 66 | 38 | 28 | -45 | 3.83E-07 | 2.40E-05 | <1.00E-04 |
| 100 | 87 | 43 | 27 | -100 | 6.88E-07 | 1.64E-05 | 4.06E-05 |
| 30 | 16 | 11 | 13 | -87 | <1.00E-08 | 1.34E-05 | 4.24E-05 |
| 22 | 8 | -6 | 3 | -75 | <1.00E-08 | | 4.79E-05 |
| -28 | -17 | -24 | -15 | -98 | <1.00E-08 | <1.00E-08 | 2.62E-05 |
| 110 | 96 | 82 | 25 | -77 | 3.66E-06 | 1.77E-05 | 5.48E-05 |
| 45 | 8 | -4 | -6 | -97 | <1.00E-08 | 4.78E-07 | 2.97E-05 |
| 8 | -12 | -21 | -19 | -29 | <1.00E-08 | 2.45E-08 | >1.00E-04 |
| -53 | -66 | -52 | -13 | -24 | <1.00E-08 | <1.00E-08 | <1.00E-08 |
| -74 | -77 | -85 | -62 | -100 | <1.00E-08 | <1.00E-08 | 3.77E-05 |
| 47 | 36 | 6 | 15 | -96 | <1.00E-08 | 1.35E-05 | |
| 35 | 27 | 25 | 19 | -87 | <1.00E-08 | 1.51E-05 | 4.48E-05 |

FIG. 15F

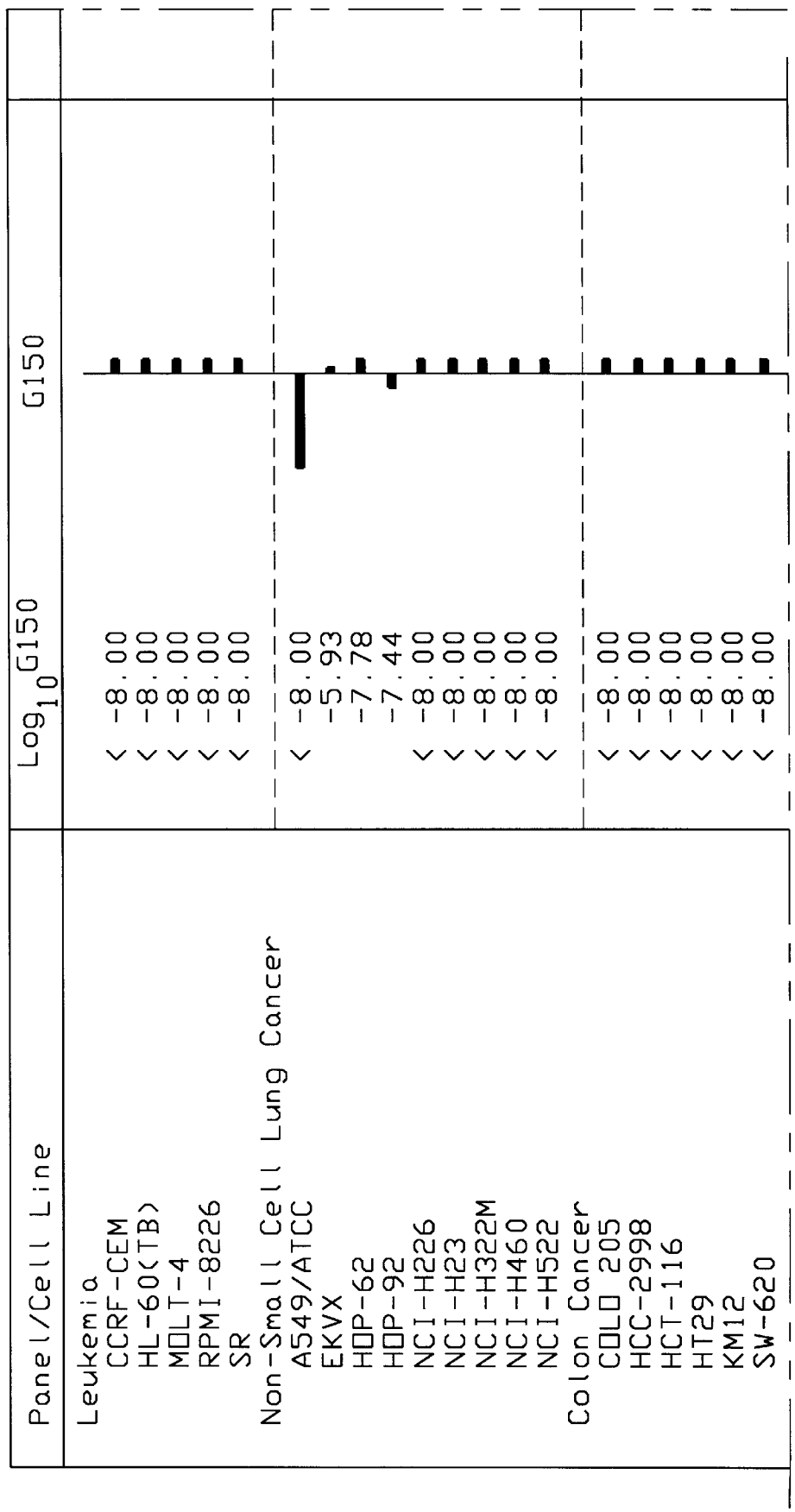
FIG. 16A "ANOLOG"

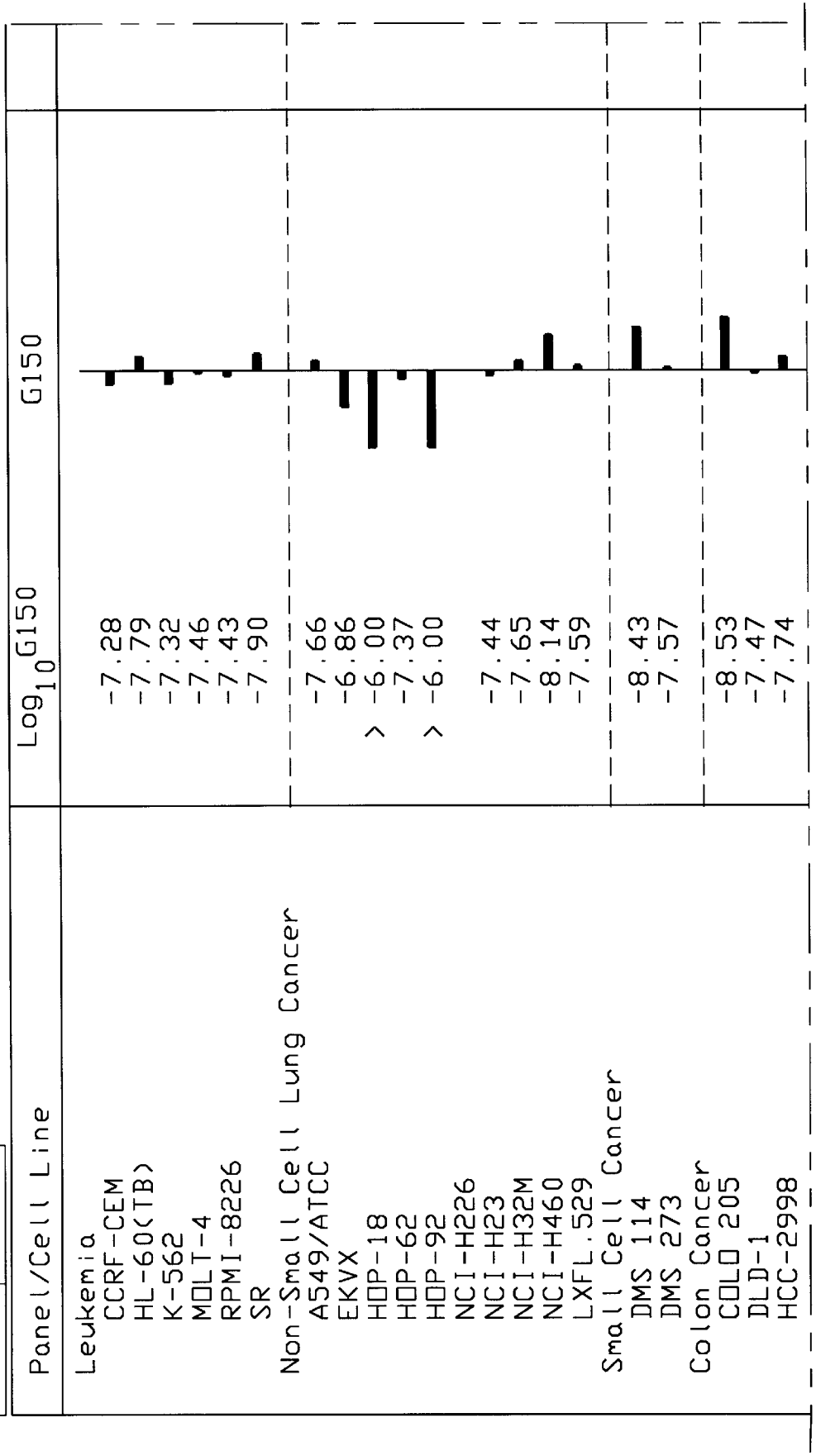
FIG. 18A "TAXOTERE"

"BACCATIN III"

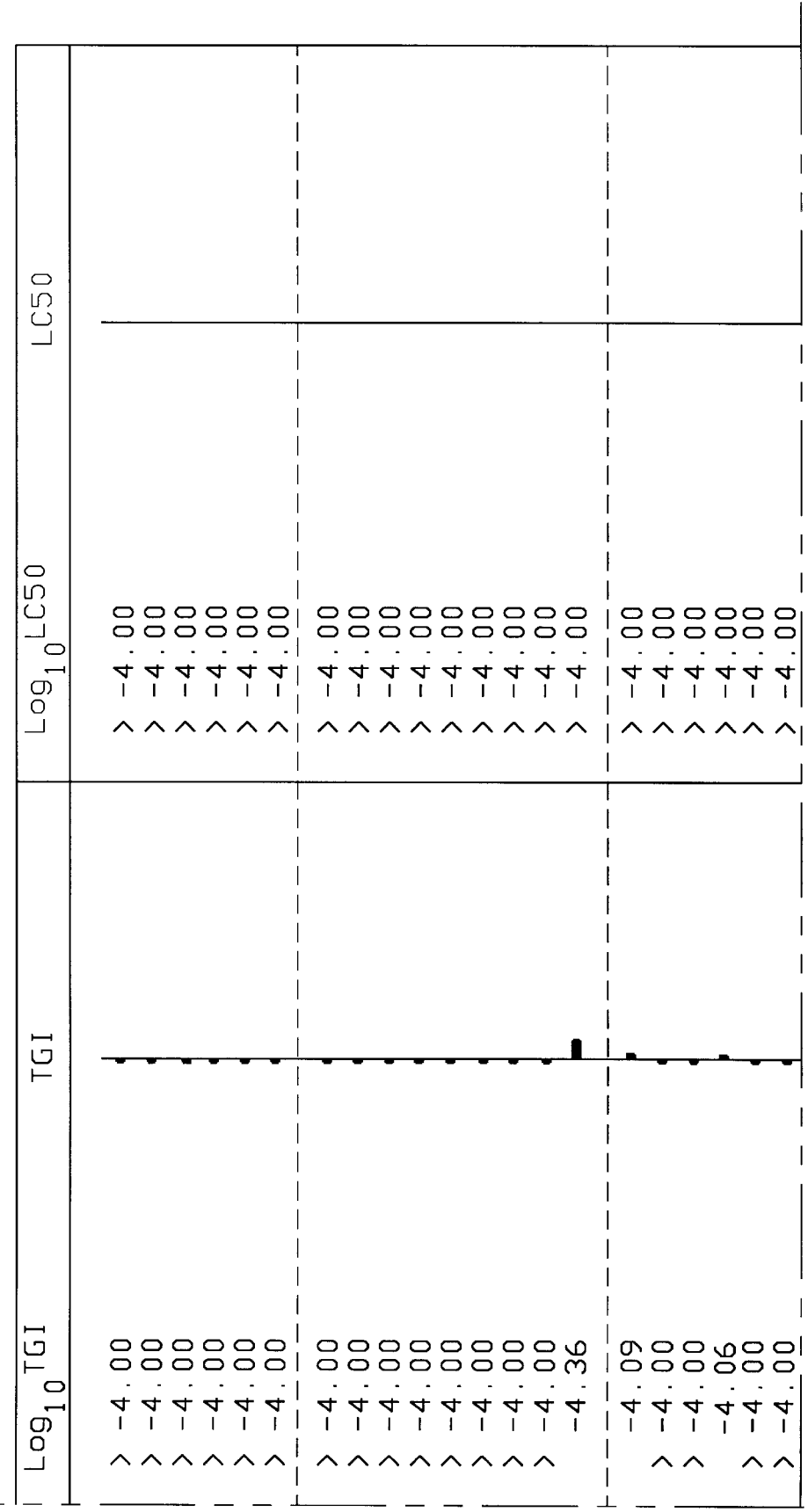

DIHALOCEPHALOMANNINE AND METHODS OF USE THEREFOR

This application is a continuation-in-part of application U.S. Ser. No. 08/530,846, filed Oct. 2, 1995, now abandoned.

FIELD OF THE INVENTION

This invention relates to halogenated cephalomannine, especially 2", 3"-dibromocephalomannine, its preparation, methods of its use as an effective antitumor agent and as an alternative to paclitaxel in bioactivity testing.

BACKGROUND OF THE INVENTION

Cephalomannine is a natural product which can be found in the bark of the pacific yew tree *Taxus brevifolia,* and such other yew species as *T. baccata, T. cuspidata,* as well as *T. yannanensis* and other plant materials including *T. hicksii, T. densiformis, T. gem, T. wardii, T. cuspidata, T. capitata, T. brownii* and *T. dark green spreader.* It can also be found in Cephalotaxus species, such as, for example, *Cephalotaxus mannii* as well as cultured plant cells and fungi. Cephalomannine is most often present with its well known and structurally similar analog, paclitaxel, the structures of both of which are shown in FIGS. 1 and 2.

Paclitaxel has been approved by the Food and Drug Administration for treatment of ovarian cancer and breast cancer. At present it is undergoing clinical trials for treatment of various other cancers.

The supply of paclitaxel, however, is limited to a finite amount of yew trees and other vegetation in which it is present in small amounts. Thus, alternative compounds having paclitaxel-like antitumor activity are highly desirable not only as an added therapeutic agent, but as a substitute for use in clinical trials so as to not deplete the valuable supply of paclitaxel.

SUMMARY OF THE INVENTION

In accordance with that above, the present invention provides novel selectively halogenated derivatives of cephalomannine which show in vitro and in vivo paclitaxel-like antitumor efficacy and methods for the preparation thereof, as well as methods for treating tumors with the novel cephalomannine derivatives. The cephalomannine derivatives are easily prepared in good yield from either complex mixtures comprising cephalomannine, paclitaxel and other taxane compounds or from more refined sources of cephalomannine by selectively halogenating, preferably brominating, the unsaturated side chain portion of the cephalomannine molecule, while leaving other portions or moieties of the molecule unchanged, as well as that of its valuable analog paclitaxel, to produce 2", 3" dihalocephalomannine, which is easily separated from the mixture, purified and available for chemotherapeutic use.

The invention is more fully described by the following Detailed Description of Preferred Embodiments and drawings.

DETAILED DESCRIPTION OF PREFERRED EMBODIMENTS

The present invention provides for the preparation of 2", 3"-dihalocephalomannine, preferably 2", 3"-dibromocephalomannine, from unpurified, partially purified or purified mixtures of cephalomannine, paclitaxel and other taxanes by reacting the mixture with bromine at a temperature and for a time sufficient to selectively brominate the unsaturated side chain portion of substantially all of the cephalomannine present, and then easily separating the resulting less polar dibromocephalomannine from paclitaxel and other taxane compounds by standard chromatographic techniques.

The method of the present invention is advantageously independent of the concentration of cephalomannine present in various complex mixtures of taxane compounds, and can utilize any source containing cephalomannine as the starting material. These sources include the bark from various Taxus species including *Taxus brevifolia, Taxus baccata, Taxus yunnanensis* and *Taxus wallichiana,* plant material such as needles and twigs from various Taxus and Cephalotaxus species, extracts of biomass containing a complex mixture of taxane type compounds, as well as in the downstream purification of cephallomannine produced from sources such as the cell culture of Taxus species and cephalomannine-producing fungi.

In the preferred method of the present invention, a mixture of taxanes, comprising paclitaxel and cephalomannine, are reacted with stoichiometric quantities of bromine diluted in an inert solvent, preferably a chlorinated solvent such as carbon tetrachloride, chloroform, methylene chloride, or ethylene dichloride.

Bromine is preferred for use in this invention because of its high efficiency and low cost and toxicity. However, the use of other halogens in this invention is also contemplated. The present invention is also effective for the selective halogenation, preferably bromination, of other taxanes containing exocyclic double bonds.

Figure 1:
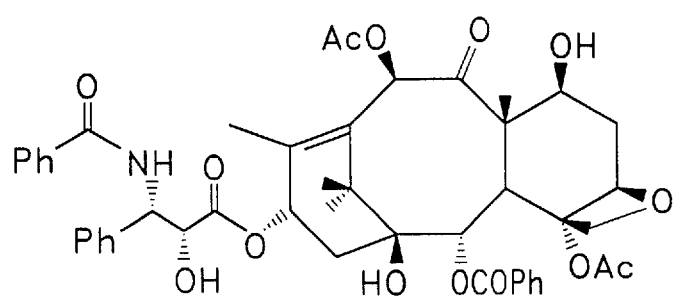
FIG. 1 illustrates a general representation of the structure of paclitaxel.
Figure 2:
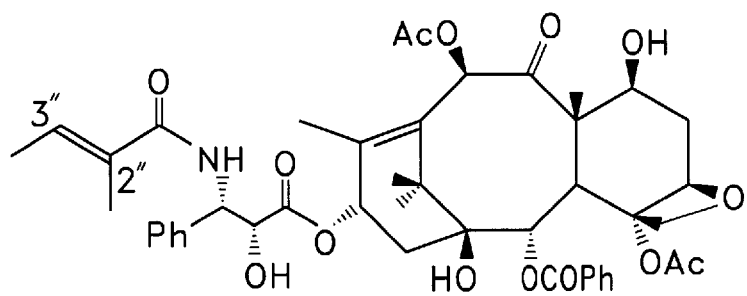
FIG. 2 illustrates a general representation of the structure of cephalomannine.
Figure 3:
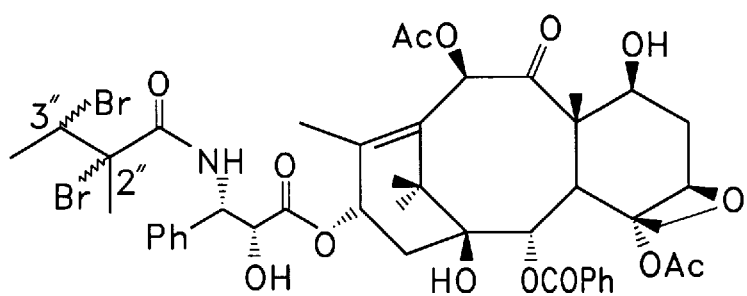
FIG. 3 illustrates a general representation of the structure of 2", 3"-dibromocephalomannine.

As shown below in one example, treatment of a mixture containing approximately 90% by weight cephalomannine in carbon tetrachloride with 1.2 molar equivalents of bromine (0.2 moles more than stoichiometric calculation) resulted in a quantitative yield of a diastereomeric mixture of 2", 3"-dibromocephalomannine. Diastereomeric dibromocephalomannine is shown in FIG. 3. The chemical structure of the diastereomeric mixture was elucidated using modern physicochemical methods, including m.p., elemental analysis, TLC, UV, IR, $^1$HNMR, $^{13}$CNMR, EI-MS, DCI-MS, FAB$^+$-MS, HPLC, TGA and DSC as also shown below.

In another example described below in detail, bromination of cephalomannine was also performed on a mixture containing approximately 30% cephalomannine, 50% paclitaxel, and 20% of other impurities (% as determined by HPLC). The sample was dissolved in a preferred halogenated solvent, for example $CCl_4$, and cooled to a range of between −5° to 5° C. and a bromine/$CCl_4$ solution added dropwise while using an ice bath to maintain temperature between −5° to 5° C. The reaction was monitored every hour by HPLC to analyze for cephalomannine and paclitaxel content. Results showed that the cephalomannine was completely brominated within 8 hours and that no degradation or reaction with paclitaxel had occurred. The reaction mixture was next washed with 0.5–1.0% $Na_2SO_3$, 0.5–1% $NaHCO_3$, and water, dried with anhydrous $Na_2SO_4$ and concentrated to a dry material. Paclitaxel and dibromocephalomannine contained in this material were then further separated and purified by column chromatography over silica gel and crystallization.

For mixtures containing cephalomannine and amounts of about 0.1–99.5% paclitaxel, (dry powders which can be white, cream, yellow, green or light brown) the process is similar that described above. The mixture is dissolved in a large amount of chlorinated solvent, preferably $CCl_4$, $CHCl_3$, $ClCH_2CH_2CL$ or $CH_2Cl_2$, and after cooling to 0° C. with stirring, stoichiometric amounts of bromine (1.2 molar equivalents) diluted with $CCl_4$ are added until the cephalomannine is completely brominated. While it is contemplated that at least some amount of dibromocephalomannine can be produced within a broad temperature range, it is preferred that the entire reaction be run in the dark at temperatures between about −20° C. to about 20° C., and most preferred at temperatures between about −5° C. to about 5° C. The reaction can be convenantly monitored, for example, by HPLC analysis.

In all cases, cephalomannine is halogenated, preferably brominated, with a high selectively to 2", 3"-dibromocephalomannine. The resulting mixtures containing paclitaxel, dibromocephalomannine and other brominated compounds can be separated and purified using a variety of conventional methods such as chromatography and crystallization. The transformation of the cephalomannine to the less polar dihalo (dibromo) derivative provides for a highly efficient and easy separation of paclitaxel from the mixture.

Figure 4:
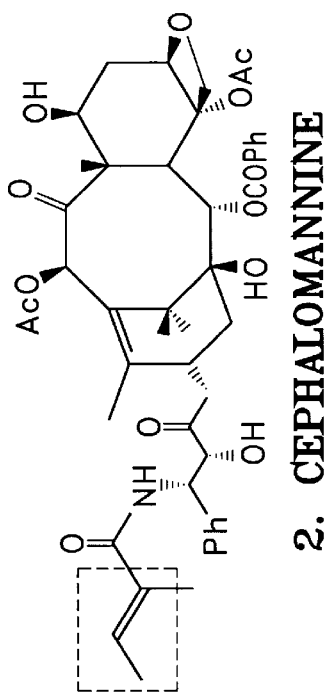
FIG. 4 illustrates a general representation of the structures of various unsaturated taxane compounds, including paclitaxel and cephalomannine.
Figure 4:
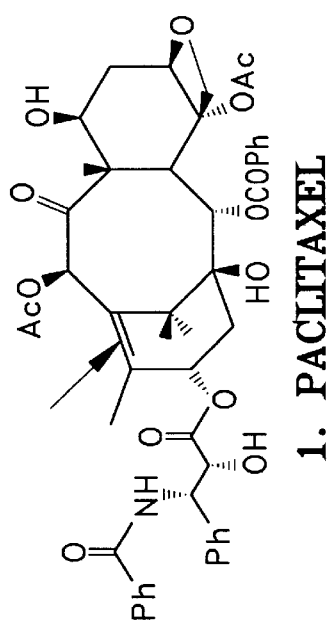
Figure 4:
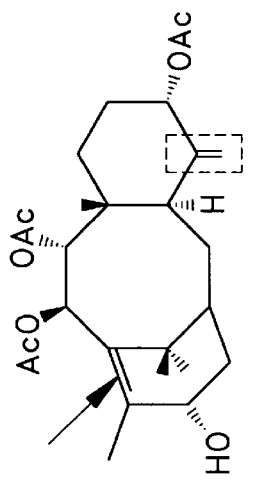
Figure 4:
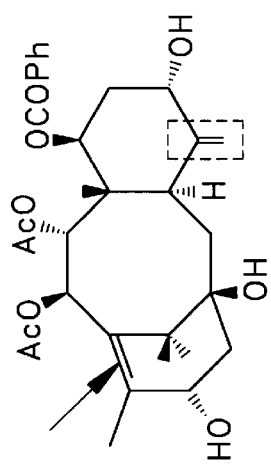
Figure 4:
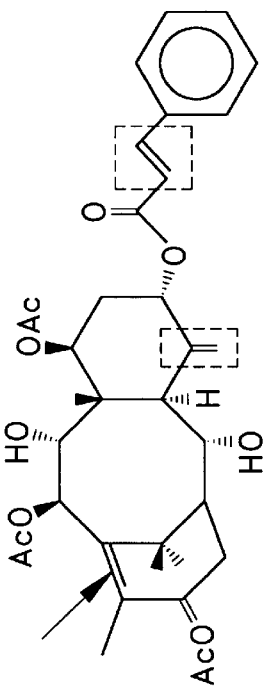
Figure 4:
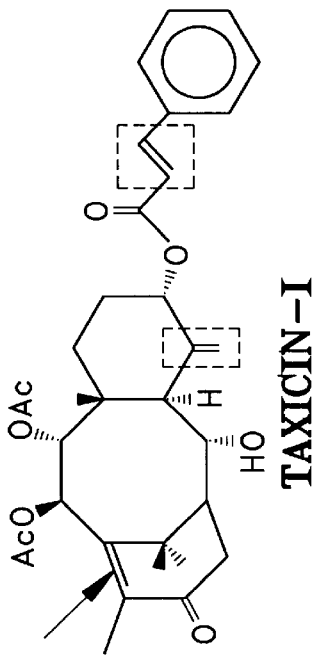

The number of molar equivalents of bromine added to the mixture depends mainly on the amount of cephalomannine present and also that of other unsaturated compounds. Generally, a less pure mixture, i.e. a mixture containing a high amount of unsaturated taxanes relative to cephalomannine, requires more molar equivalents of halogen such as bromine to completely brominate the cephalomannine than a purer mixture would require. FIG. 4 lists various exocyclic unsaturated taxanes that can be present in a mixture along with cephalomannine and paclitaxel. Thus, if a mixture has a high content of exocyclic unsaturated compounds such as taxusin, taxicin-I, taxinin and brevifoliol such as shown in FIG. 4, required molar equivalents of bromine will be higher, as such compounds will absorb more than the stoichiometric 1.2 molar equivalents of bromine required for conversion to dibromocephalomannine.

Solvents that can be used for the process of bromination in this invention must be inert to bromine (or other halogens as the case may be). The most useful and preferred solvents are chlorinated solvents such as $CCl_4$, $CHCl_3$, $ClCH_2CH_2Cl$ and $CH_2Cl_2$, with $CCl_4$ being the most preferred. The most preferred source for bromination of cephalomannine in accordance with this invention is 0.01–0.1M bromine in carbon tetrachloride or chloroform which is commercially available.

Conventional wisdom would lead one to expect that the use of halogen, such as bromine, to brominate taxane compounds containing several functional groups sensitive to bromine would inevitably result in some reactions undesirably occurring with paclitaxel, for example, with its cyclic double bond or bromination of positions on the taxane ring (or the same with cephalomannine for that matter) or with other compounds listed in FIG. 4. However, in accordance with this invention it has been surprisingly and unexpectedly found that selectivity for bromination of the 2", 3" positions of the unsaturated side chain portion of cephalomannine is very high. In the process of the invention, paclitaxel is neither significantly degraded nor brominated during the reaction. It is possible that paclitaxel may degrade to several unidentified compounds if the reaction is exposed to excessive light, or if an excessive amount of bromine is employed. However, such an undesirable occurrence can be easily averted; any degradation of paclitaxel during bromination can be avoided and the proper conditions adjusted appropriately without undue experimentation by periodically monitoring the reaction, for example, by HPLC.

The following examples are provided to illustrate preferred embodiments for selective bromination of samples containing cephalomannine, paclitaxel and other taxanes in different ratios, without significant degradation of paclitaxel. It is to be understood, however, that these examples are only intended to illustrate some preferred embodiments of the invention, and are not in any way intended to limit the scope or spirit of the invention as defined in the claims.

EXAMPLE 1

Procedure for the Bromination of Partially Purified Cephalomannine

A solution of 0.63 g 91.5% cephalomannine (0.0007 moles), also containing about 6–7% paclitaxel, dissolved in 150 mL carbon tetrachloride was added to a 500 mL three neck round bottom flask, fitted with a 250 mL separatory funnel. The flask was immersed in an ice-salt bath. When the temperature reached −5° C., a solution of bromine (0.1221 g) in carbon tetrachloride (76.31 mL, 0.01M) was added slowly with stirring at such a rate that the reaction temperature did not exceed 5° C. The cephalomannine to bromine ratio was 1:1.1 mole. The addition required about three hours and the resulting solution was light brown and cloudy.

The bromination was monitored by HPLC analysis every hour. The reaction was completed when all the cephalomannine present was converted to the 2", 3"-dibromoderivative, which, based on HPLC analysis, required approximately 8 hrs. The reaction mixture was light yellow to colorless, due to the consumption of the bromine, in contrast to the darker starting solution.

The reaction mixture was then transferred to a one litre separatory funnel and first washed with 0.5% aqueous sodium sulfite (300 mL), 0.5% aqueous sodium bicarbonate (300 mL) and then twice with deionized water (200 mL each) to a final pH 6.5. The combined aqueous layer was extracted once with $CH_2Cl_2$ and the $CH_2Cl_2$ layer mixed with the previous organic extract. The organic layer was next dried over $Na_2SO_4$, filtered, and evaporated to dryness. The yield was 0.76 g of a light cream-colored solid which is approximately a 100% yield based on the starting material.

The cream colored solid material was chromatographed on a column of silica gel (50 g, ICN Silitech, 32–63 D, 60 A) using the solvent mixture acetone:$CH_2Cl_2$ (10:90) as the eluent. Fifty mL fractions were collected and checked by TLC (Silica gel 60 $F_{254}$, Merck #5554, developed with acetone/$CH_2Cl_2$: 20/80, detected using vanillin-sulfuric acid in methanol spray reagent). The fractions with a single spot at $R_f$=0.64 (fractions #26–#38) were mixed, concentrated to dryness to yield 0.485 g of a light cream powder, which was recrystallized to white crystalline solid, mp 158° C., and identified as 2", 3"-dibromocephalomannine by physicochemical methods (TLC, HPLC, UV, IR, NMR, MS). The yield was estimated to be 70% on the basis of starting cephalomannine.

EXAMPLE 2

Procedure for the Bromination of a Crude Mixture Containing Cephalomannine, Paclitaxel and Other Taxane-Type Compounds Using similar apparatus as used in Example 1, a sample of crude paclitaxel (2.0 g) having a mixture of 51.2% paclitaxel 28.8% cephalomannine, and about 20% other taxanes or non-taxane impurities based on HPLC was dissolved in 150 mL carbon tetrachloride and 150 mL $CH_2Cl_2$, to yield a clear, light yellow solution. The flask was immersed in an ice-salt bath and stirred. When the temperature reached −5° C., a solution of 0.1332 g 100% bromine in 83.13 mL (0.01M) of carbon tetrachloride (1 mole cephalomannine: 1.2 moles bromine) was added to the solution at such a rate that the temperature of the reaction mixture did not exceed 5° C. The addition required about three hours and resulted in a cloudy, brownish-yellow solution. After the addition of bromine was completed, the reaction was allowed to continue under the same conditions for an additional 8 hours, with HPLC analyses of the paclitaxel and cephalomannine performed every hour. The reaction is complete when the solution is colorless or light yellow and all the cephalomannine has been converted to the dibromo derivative. If after the additional 8 hours the solution still contains more than 1–2% cephalomannine, keeping the initial conditions, 10 mL 0.01M bromine in carbon tetrachloride is added dropwise and allowed to react for 1 hour before analyzing again with HPLC.

Excess bromine from the reaction mixture was removed by washing with 0.5% aqueous $Na_2SO_3$ (300 mL), 0.5% aqueous $NaHCO_3$ (200 mL), and deionized water (2×200 mL). The reaction mixture was dried using anhydrous $Na_2SO_4$ and concentrated to dryness under high vacuum to yield 2.35 g of dry light cream to white powder. The dry material was then purified on a silica gel column under the conditions listed in Example 1. The ratio between the mixture to be separated and the silica gel was 1:60, thus 120 g silica gel were used. Each fraction was checked by TLC and every third fraction by HPLC. Fractions with the same $R_f$ in TLC and same retention time in HPLC were mixed to afford two combined fractions. Fractions (#25–#39) which showed a single TLC spot with $R_f$ 0.64 represented dibromocephalomannine and fractions (#41–#81) which showed a single TLC spot with $R_f$ 0.49 represented paclitaxel.

Fractions #25–#39, after concentration to dryness at about 40° C. under high vacuum, yielded a white to light yellow solid, 0.460 g, (66.6% theoretical yield) with a m.p. 158°–160° C. (chromatographic purity 96.19%) as determined by TLC.

TLC materials were employed as follows: $R_f$=0.64 (single spot) on Silica gel 60 $F_{254}$ Plate (Merck, #5554)

Solvent system: acetone: $CH_2Cl_2$ (20:80)

Spray Reagent: Vanilin/Sulfuric Acid in Methanol

Mass Spectrum [FAB]$^+$ of the obtained dibromocephalomannine:

[M+H]$^+$=990, 992, 994

[M+Na]$^+$=1014

[M+K]$^+$=1030

Concentration of the second combined fractions (#41–#81) yielded 1.16 g (>100% theoretical yield) paclitaxel, which was recrystallized using 50:50 acetone/hexane, filtered, washed with the same ratio of cooled solvent and dried under high vacuum at 40° C. for 24 h. The yield was 0.902 g (45.11% theoretical based on the HPLC analysis of paclitaxel in the starting material) of a white crystalline material with a m.p. of 214° C.–216° C.

TLC analysis materials: $R_f$=0.49 in the presence of authentic sample on silica gel 60 $F_{254}$ plate [Merck #5554]

Solvent system: Acetone/$CH_2Cl_2$ (20:80)

Spray Reagent: Vanilin/Sulfuric Acid in Methanol

Both the UV and the IR spectra of the resulting material match those of pure paclitaxel which demonstrates the high selectivity of the bromination reaction for the 2", 3" unsaturated side chain positions of cephalomannine, leaving its close analog paclitaxel untouched.

EXAMPLE 3

A Scaled-Up Example Illustrating the Bromination of a Crude Mixture Containing Cephalomannine A solution of 10.00 g crude paclitaxel (on the basis of HPLC analysis the content was 28.8% cephalomannine, 51.2% paclitaxel and approximately 20% other taxane or non-taxane impurities) was dissolved in 1.5 L carbon tetrachloride in a 2.0 L three-necked flask fitted with a 500 mL separatory funnel, reflux condenser, thermometer and magnetic stirrer and immersed in an ice-salt bath. The reaction mixture was stirred until the temperature reached −5° C. and then 41.2 mL of 0.1M bromine (0.665 g bromine) in carbon tetrachloride was added dropwise for about 3 hours. The molar ratio between cephalomannine and bromine was 1:1.2. The temperature did not exceed 5° C. After the bromine addition was completed, stirring was continued while maintaining the temperature at −1° C. to 5° C. The reaction was monitored by HPLC every hour until all the cephalomannine had been converted to the dibromo derivatives (approximately 8 hrs.). The final color of the 1500–1600 mL of solution was light yellow or cream, depending on the color of the starting mixture and the possible presence of a small excess of bromine.

To remove any trace of bromine, the reaction mixture was washed with 0.5% aqueous $Na_2SO_3$ (500 mL), 0.5% aqueous $NaHCO_3$ (500 mL), and deionized water (2×500 mL). The reaction mixture was dried with anhydrous $Na_2SO_4$, and concentrated to dryness under vacuum to yield 13.20 g of a light cream to white solid material.

This material was chromatographically separated on silica gel column under the conditions listed above in Examples 1 and 2. A 100×5 cm glass column was prepared by the slurry method with 600 g silica gel (ratio 1:50). The column was eluted with acetone/$CH_2Cl_2$ (10:90). A 1 L acetone/$CH_2Cl_2$ (25:75) was used as a final column wash. Every fraction was analyzed by TLC and every third fraction by HPLC. Fractions #11–#22 had a single spot at $R_f$=0.64 and their combination, concentration and drying (40° C., high vacuum), yielded 3.25 g (95%) of 2",3"-dibromocephalomannine as a white to light yellow solid.

Analysis of this compound is as follows:

m.p.: 158°–160° C. $R_f$=0.64 (single spot) on silica gel 60 $F_{254}$ plate [Merck #5554].

Solvent system: Acetone/$CH_2Cl_2$ (20:80)

Spray Reagent: Vanilin/Sulfuric Acid in Methanol.

Elemental Composition and Molecular Weight (on the basis of HR FAB$^+$)

$C_{45}H_{54}NO_{14}{}^{79}Br_2$ [M+H]$^+$: Calculated: 990.191000 Found: 990.191103 ($\Delta$m=0.1 ppm)

$C_{45}H_{54}NO_{14}{}^{79}Br^{81}Br$ [M+H]$^+$: Calculated: 992.181000 Found: 992.189057 ($\Delta$m=8.1 ppm)

$C_{45}H_{54}NO_{14}{}^{81}Br_2$ [M+H]$^+$: Calculated: 994.175000 Found: 994.187011 ($\Delta$m=12.1 ppm)

$C_{45}H_{53}NO_{14}Na^{79}Br^{81}Br$ [M+Na]$^+$: Calculated: 1014.161000 Found: 1014.171002 ($\Delta$m=9.9 ppm)

$C_{45}H_{53}NO_{14}K^{79}Br^{81}Br$ [M+K]$^+$: Calculated: 1030.097000 Found: 1030.144940 ($\Delta$m=46.5 ppm)

$[\alpha]_D^{25}$=−40.207° (c 0.29, MeOH)

---

Figure 5:
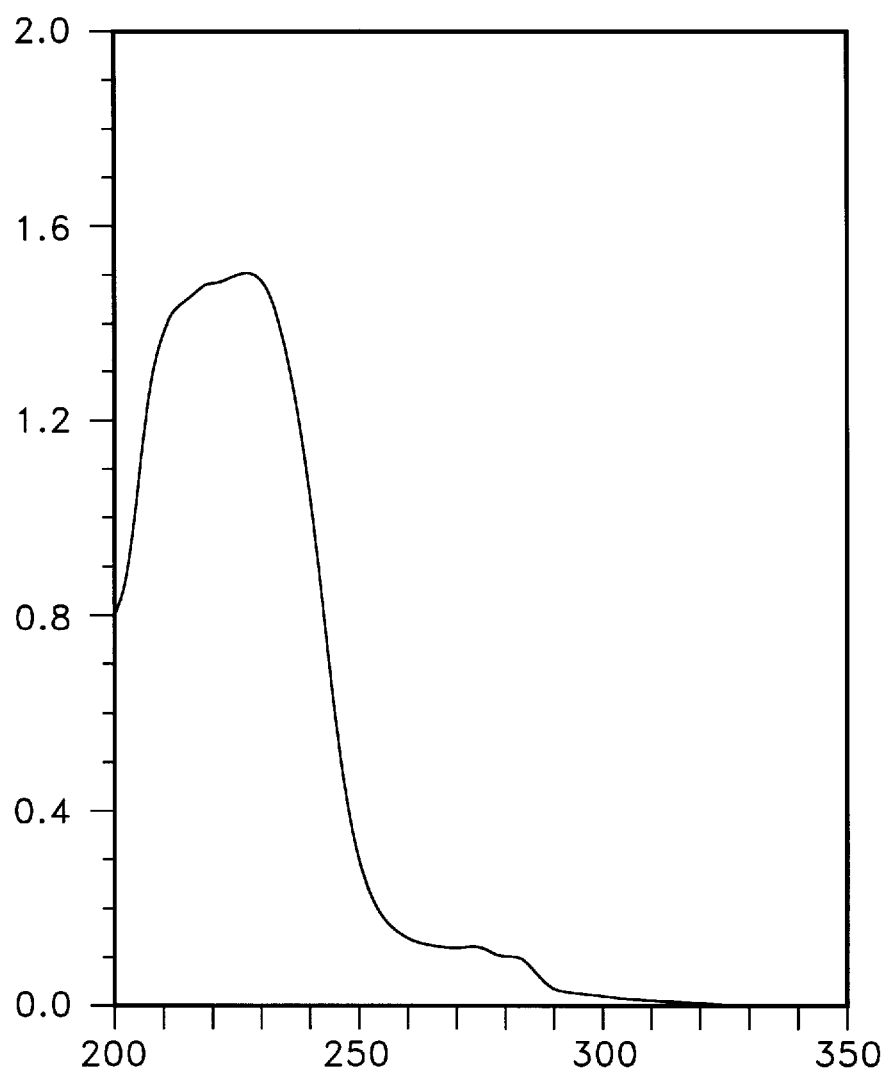
FIG. 5 is a UV spectrum of 2", 3"-dibromocephalomannine obtained from this invention.

FIG. 5
UV Spectrum in $CH_3OH$: 274.2 (1550.8); 227.1 (18610.4); 221.8 (18325.1)
 [$\lambda_{max}$ nm, ($\epsilon$)]

Figure 6:
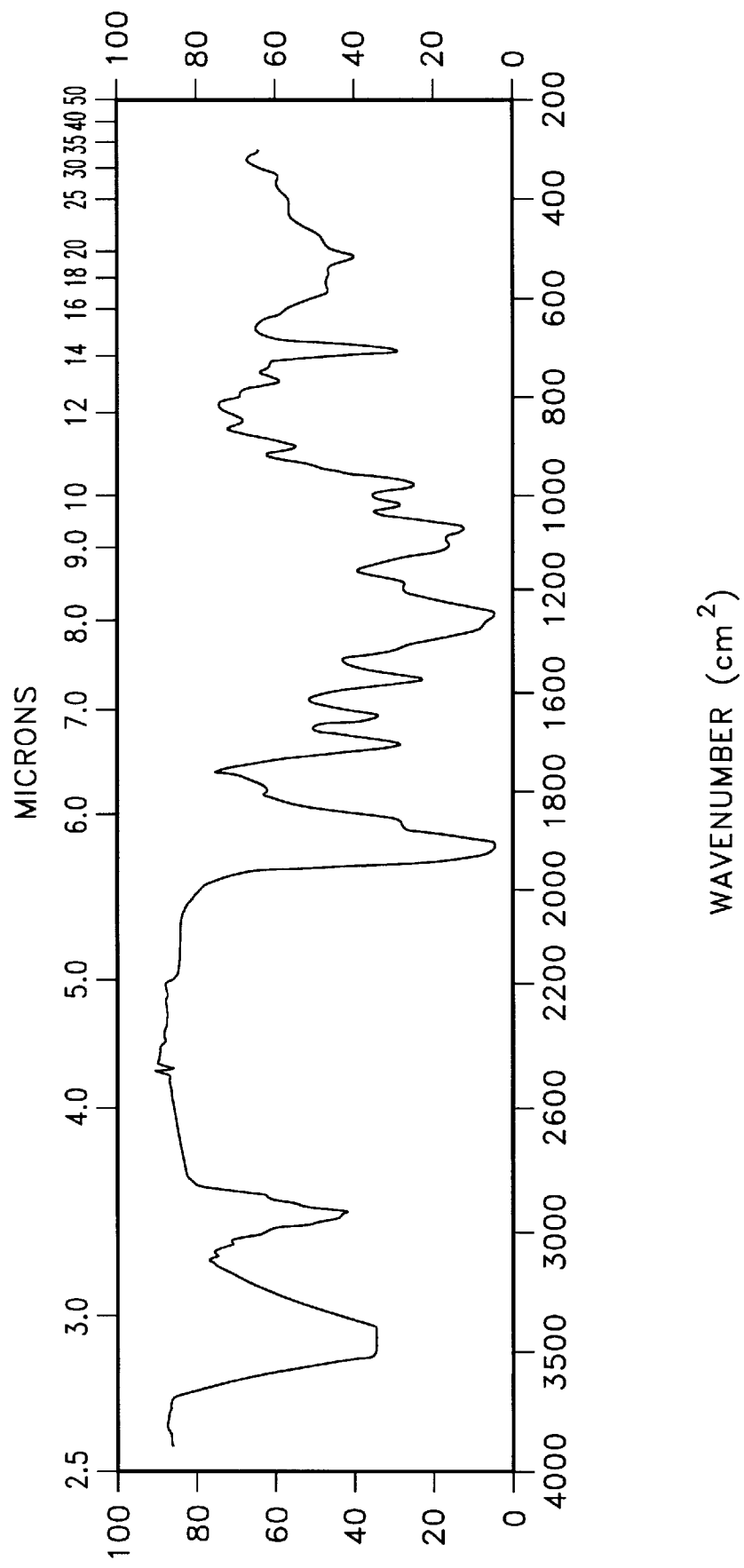
FIG. 6 is an IR spectrum of 2", 3"-dibromocephalomannine obtained from this invention.

FIG. 6
IR Spectrum in KBr (cm$^{-1}$)  3500, 1105, 1070 (tert & sec OH)
3420, 1670, 1580 (—CONH—)
3110, 3060, 1605, 1505, 770, 710 (monosubt. aromatic cpds.)
3060, 2960, 2915, 2870, 1465, 1370 (—$CH_3$, —$CH_2$—, =CH—)
3020, 1670, 1310, 980 (double bond)
1730, 1270 (aromatic esters)
1715, 1240 (>C=O)
1730, 1180 (acetates)
855 (epoxy rings)
520 (bromo compounds)

Figure 7:
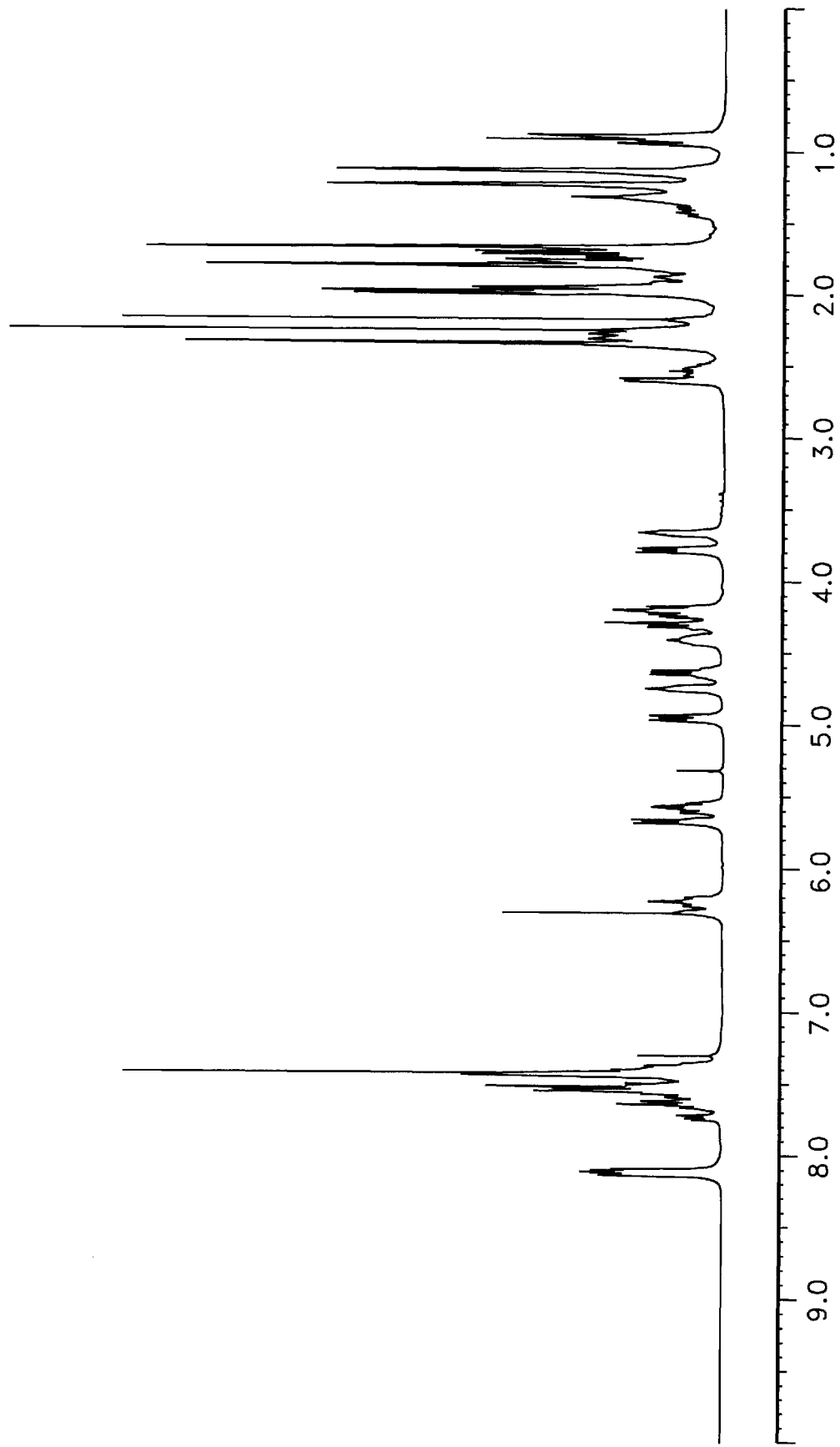
FIG. 7 is a $^1$H-NMR spectrum of 2", 3"-dibromocephalomannine obtained from this invention.

FIG. 7
$^1$H NMR in $CDCl_3$ (300 MHz): 1.98(s,3H,—COC(B$_r$)$\underline{CH}_3$-5"
(ppm; side chain protons only) 1.80(d,3H,—HC(B$_r$)$\underline{CH}_3$-4")
4.63(qt,1H,>$\underline{CH}$(B$_r$)-3")

Figure 8:
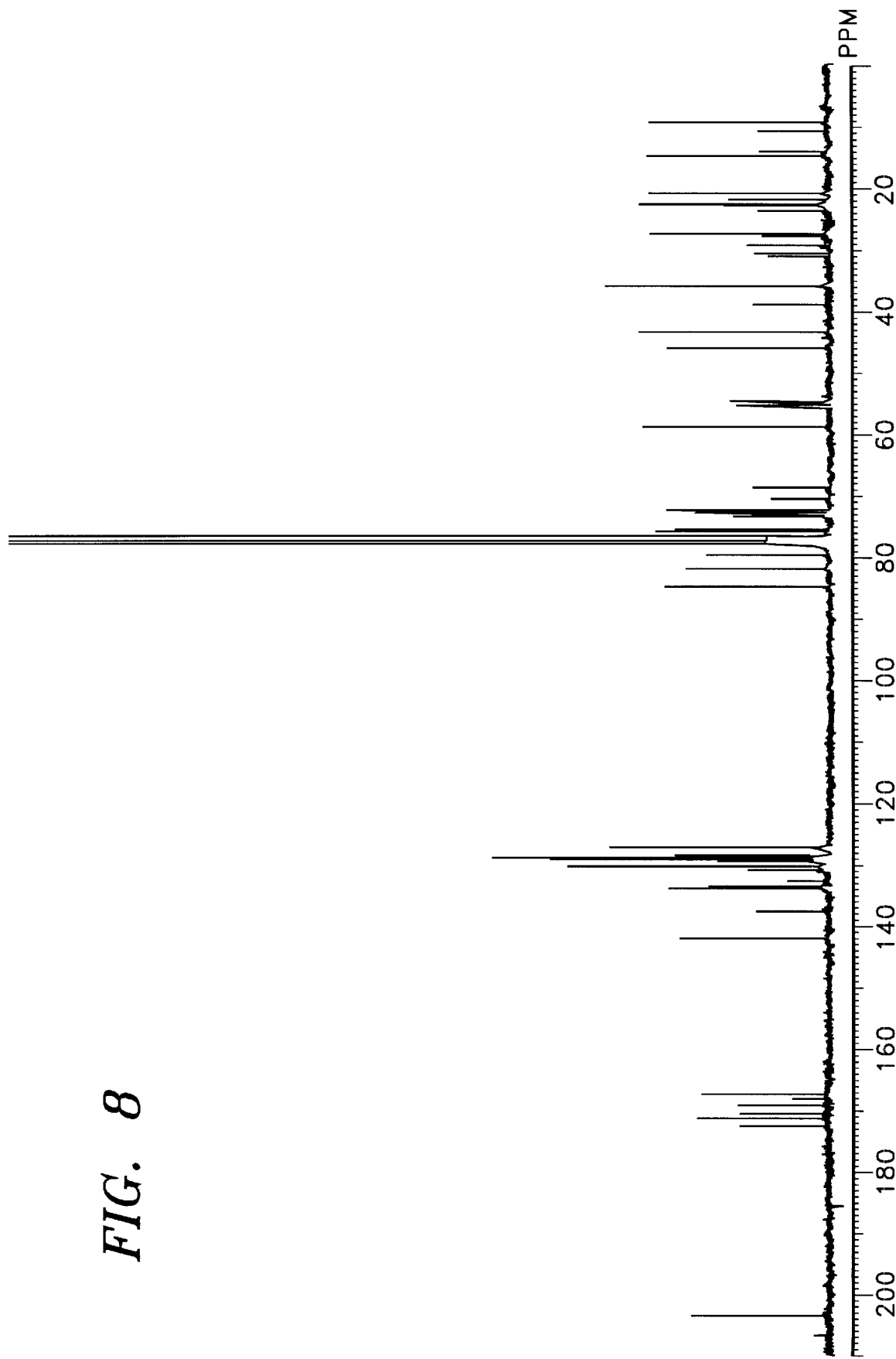
FIG. 8 is a $^{13}$C-NMR spectrum of 2", 3"-dibromocephalomannine obtained from this invention.

FIG. 8
$^{13}$C NMR (300 MHz) 172.50(C-1')
(in ppm; side-chain C only) 168.80(C-1")
72.9(C-2')
58.80(C-2")
54.5(C-3')
55.3(C-3")
22.70(C-4")
27.6(C-5")

Figure 9:
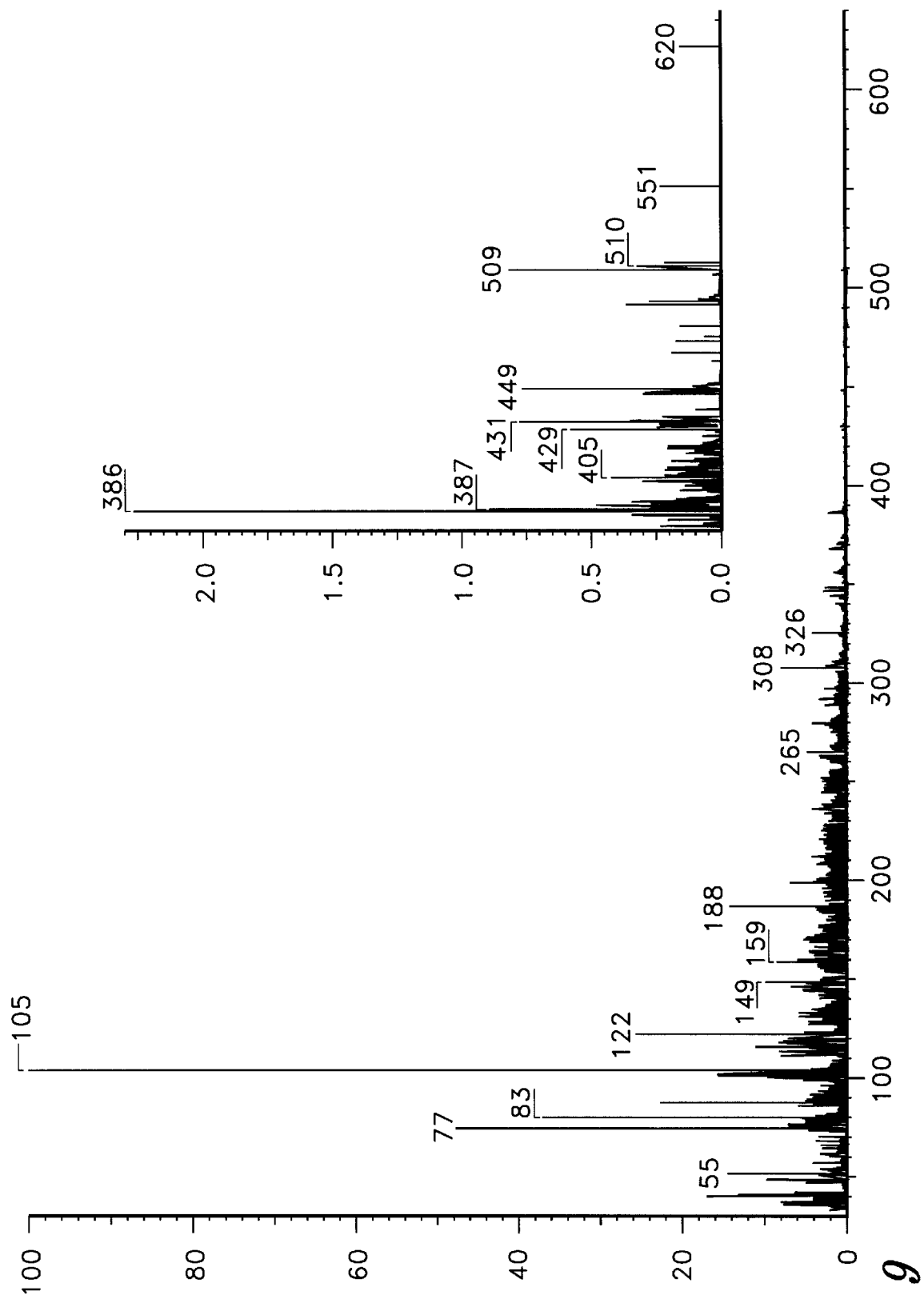
FIG. 9 is an EI-MS spectrum of 2", 3"-dibromocephalomannine obtained from this invention.

FIG. 9
EI—MS 568, 551, 509, 491, 449, 431, 405, 391, 386, 329,
(m/z) (the main fragments) 326, 308, 278, 264, 245, 217, 200, 188, 159, 149,
122, 105, 91, 83, 77, 55, 43.

Figure 10:
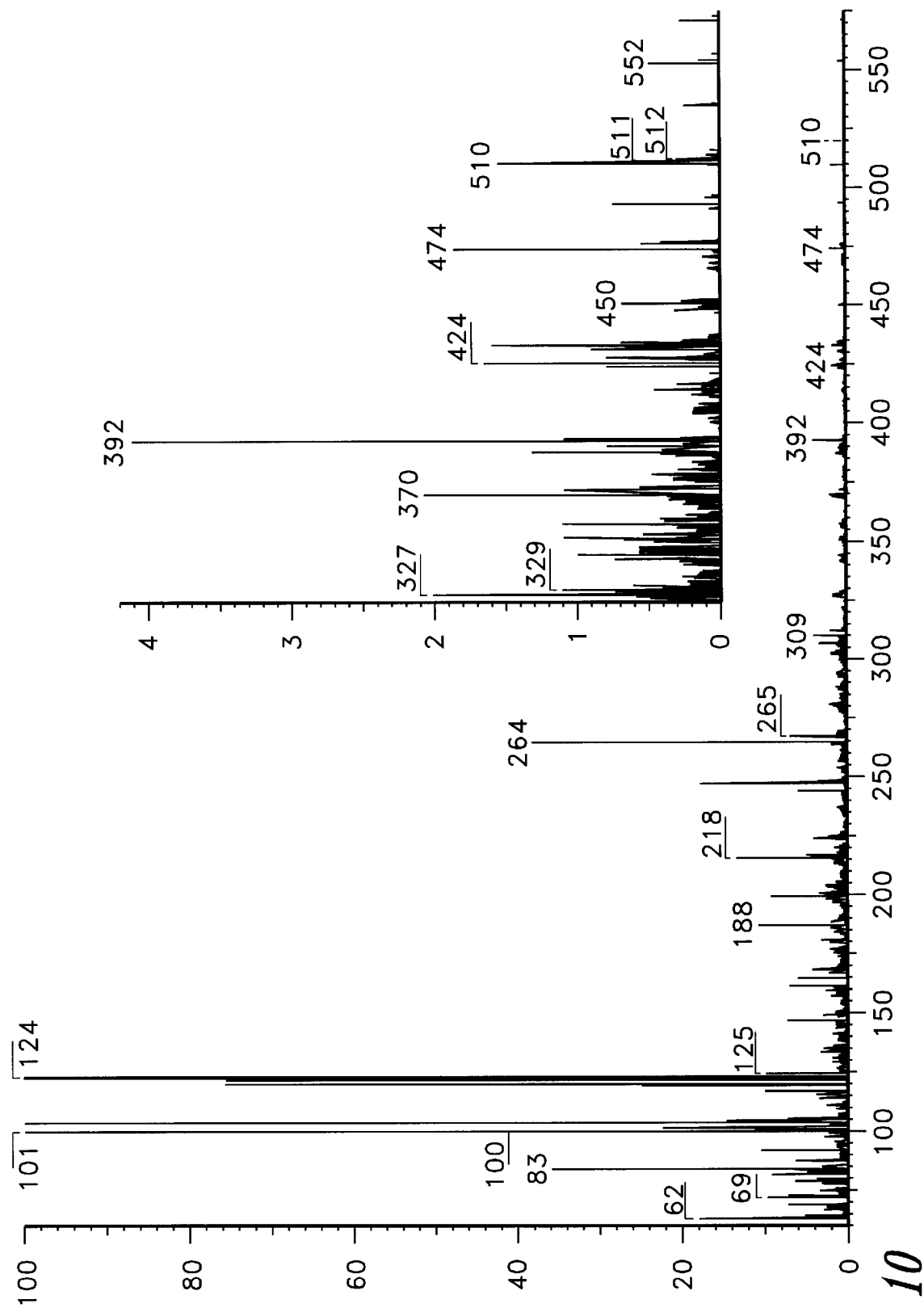
FIG. 10 is an DCI-MS spectrum of 2", 3"-dibromocephalomannine obtained from this invention.

FIG. 10
DCI—MS 569, 552, 510, 492, 474, 450, 432, 424, 392, 387, 370,
(m/z) (the main fragments) 329, 327, 309, 279, 265, 264, 246, 218, 200, 188, 167,
149, 125, 124, 106, 101, 100, 91, 83, 69.

Figure 11:
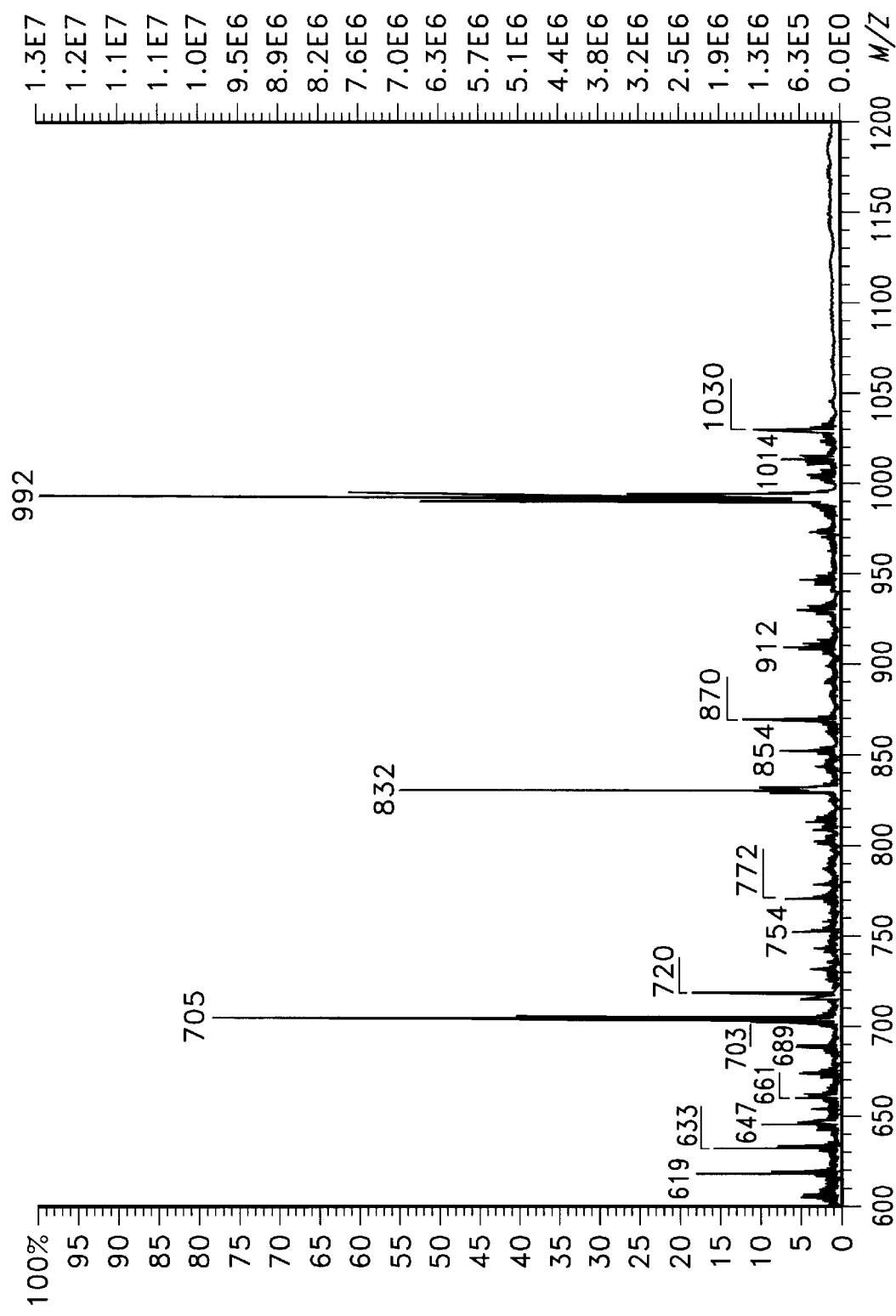
FIG. 11 is a FAB$^+$-MS spectrum of 2", 3"-dibromocephalomannine obtained from this invention.

FIG. 11
FAB—MS: (positive ion mode) 1030 [M + K]$^+$; 1014 [M + Na]$^+$; 992 [M + H]$^+$
(m/z) (See Elem. Anal.); 974 [M—H$_2$O]$^+$; 932 [M—AcOH]$^+$;
914 [M—AcOH—H$_2$O]$^+$; 912 [M—HBr]$^+$; 870
[M—BzOH]$^+$; 854 [870-H$_2$O—2H]; 832 [M2—HBr]$^+$;
705 [M-243-Ac]$^+$; 569 [T]$^+$; 551 [T—H$_2$O];
509 [T—AcOH]$^+$; 491 [T—AcOH—H$_2$O]$^+$; 448 [T—BzOH]$^+$;
429; 424[SH$_2$]$^+$; 413; 405[S—H$_2$O]$^+$; 391
[S—O—H$_2$O]$^+$; 387 [T—AcOH—BzOH]$^+$; 376; 347
[S—O—CO—HCHO]$^+$; 338:327 [387-T—
AcOH]$^+$; 315; 284[327-Ac]$^+$; 279; 264 [832-T]$^+$ or
[424-2HBr]$^+$; 246 [264-H$_2$O]$^+$; 231; 218 [264-HCOOH]$^+$;
188; 167[S—$C_5H_8ONBr_2$]$^+$; 149[167-H$_2$O]$^+$;
133; 122[BzOH]$^+$; 113:105[Bz]$^+$; 91[$C_7H_7$]$^+$;
83; 77 [$C_6H_6$]$^+$; 76; 57; 55;

-continued (T = taxane ring in the compound; S-acid (side) chain in the compound.)

Figure 12A:
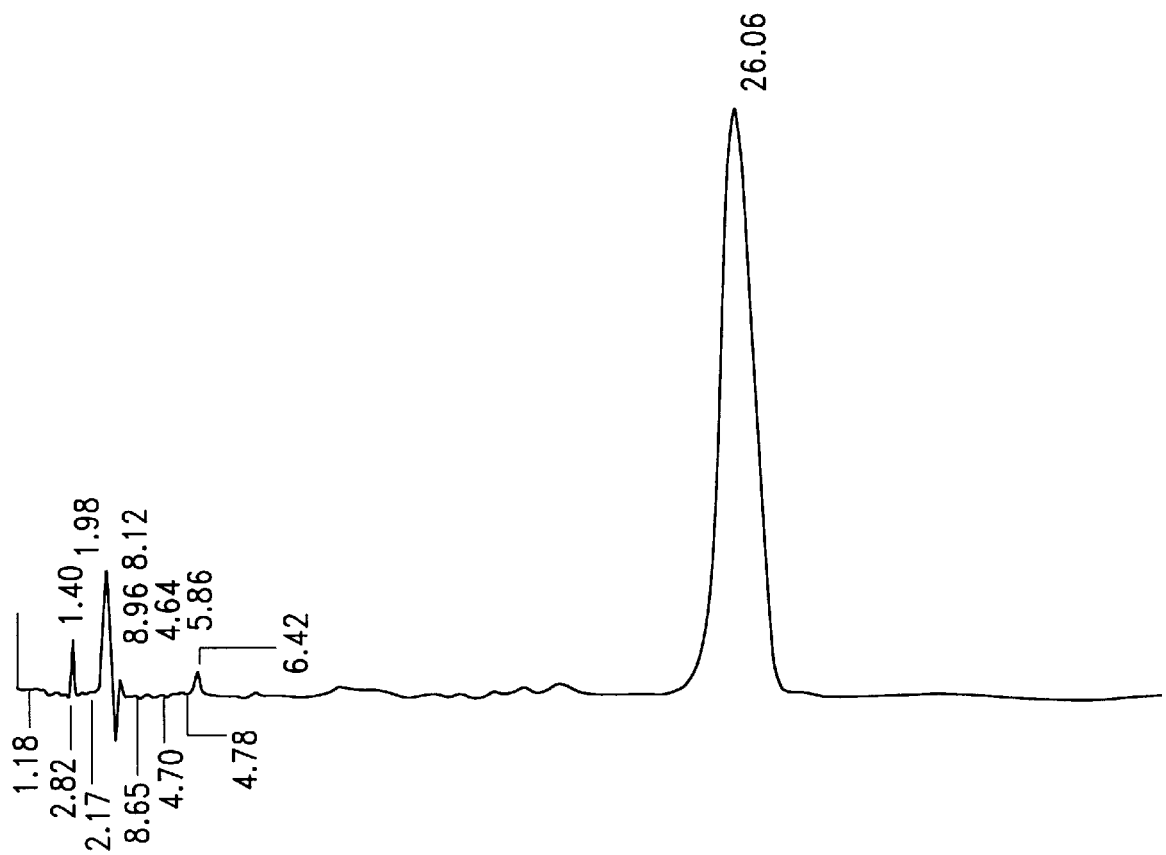
FIGS. 12a and 12b are HPLC analyses of 2", 3"-dibromocephalomannine obtained from this invention.

HPLC:
FIG. 12a
Condition 1:
| | | |
|---|---|---|
| | Column | CN 10μ(250 × 4.6 mmn) |
| | Solvent System | CH₃CN:H₂O(40:60) |
| | Flow Rate | 1 mL/min |
| | Detector | Waters 490 uv at 227 nm |
| | Injection volume | 20 μL |
| | RT$_{2'',3''\text{-dibromocephalomannine}}$ | 26.06 min. |

Figure 12B:
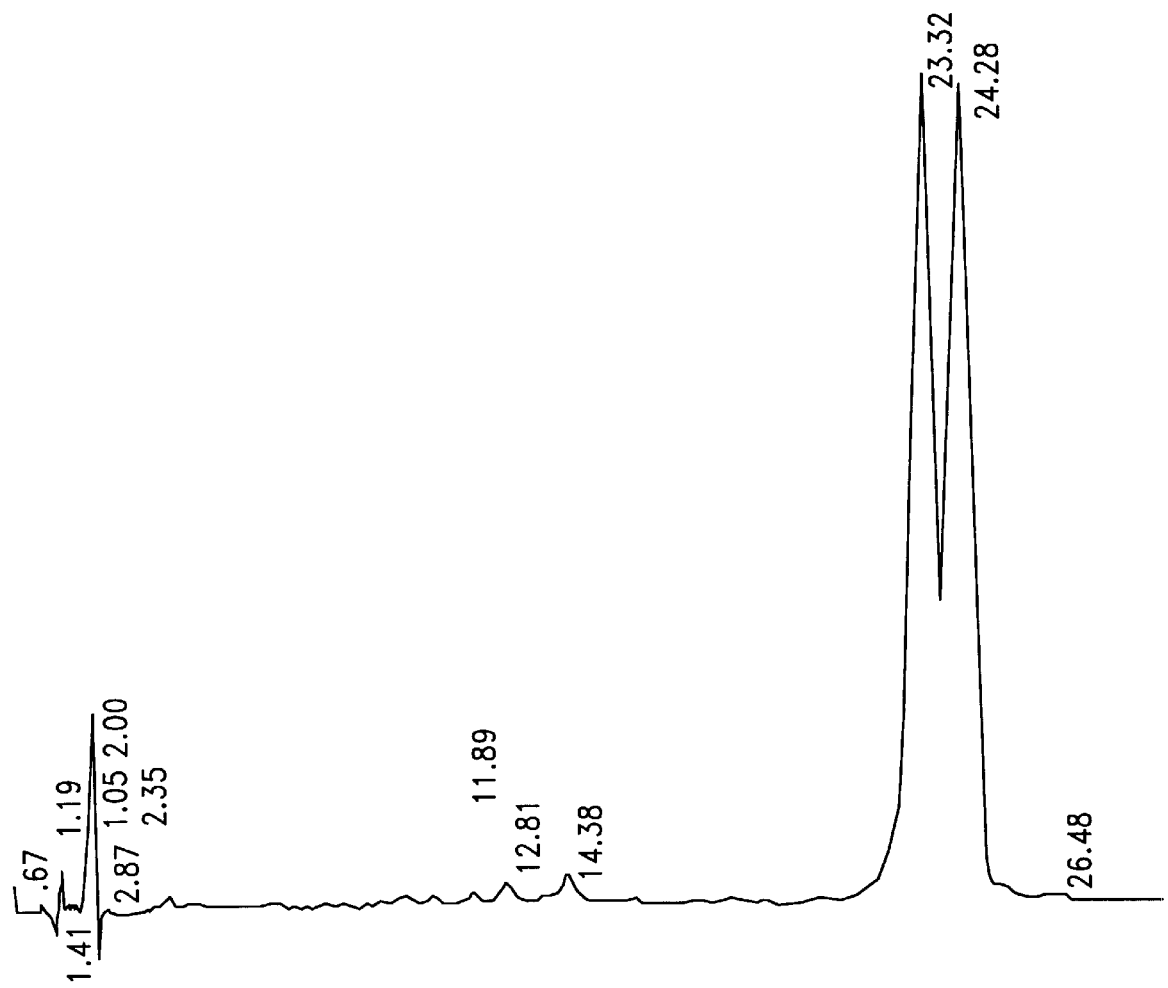

FIG. 12b
Condition 2:
| | | |
|---|---|---|
| | Column | Curosil G 6μ (250 × 3.2 mm) |
| | Solvent System | CH₃CN:H₂O (45:55) |
| | Flow Rate | 0.75 mL/min |
| | Detector | Waters 490 uv at 227 nm |
| | Injection Volume | 20 μL |
| | RT$_{2'',3''\text{-dibromocephalomannine}}$ | 2 diastereomeric forms: |
| | RT$_I$ = 23.53 | |
| | RT$_{II}$ = 24.50 | |

Figure 13:
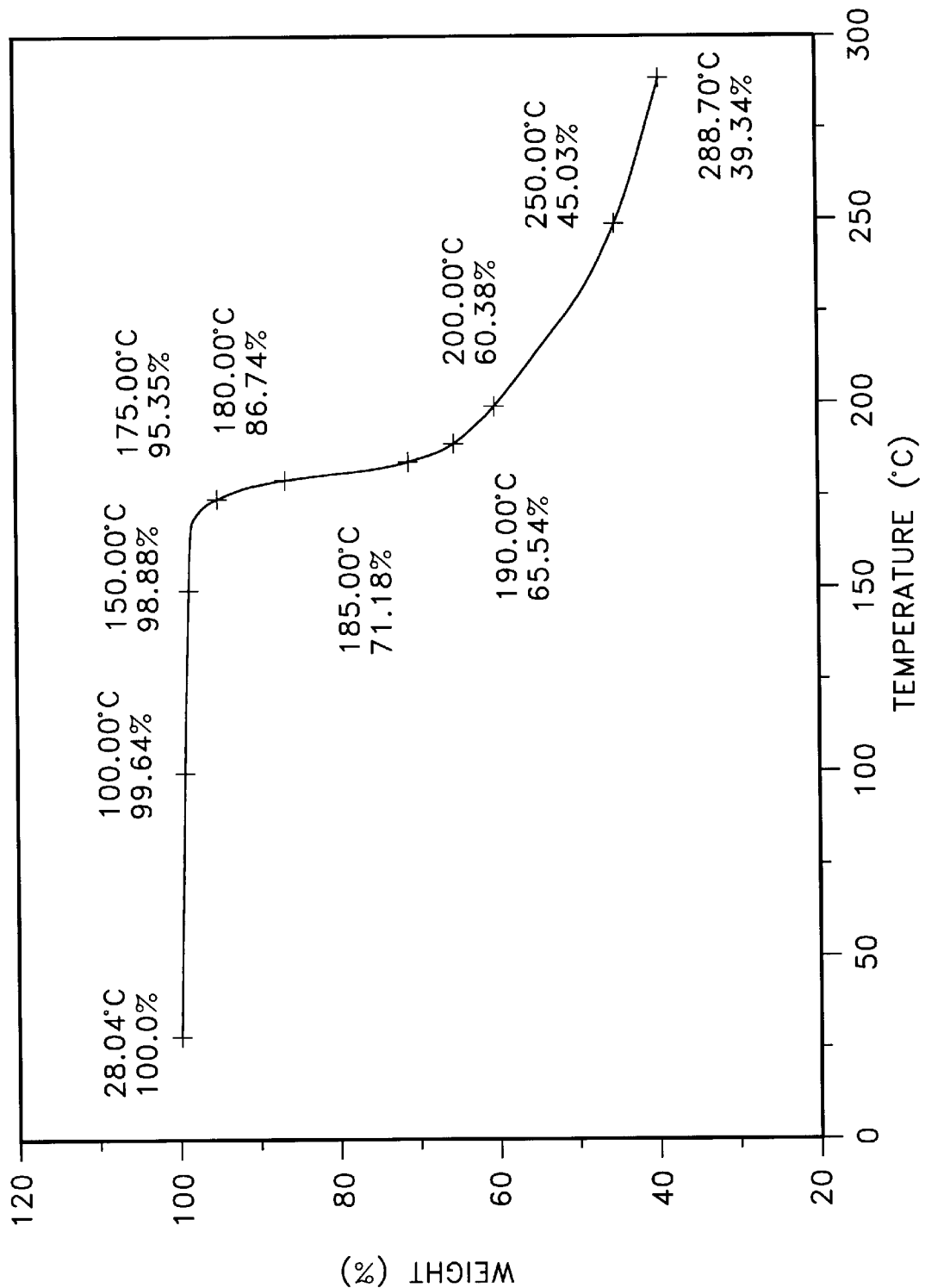
FIG. 13 is a TGA of 2", 3"-dibromocephalomannine obtained from this invention.

FIG. 13
Thermogravimetric Analysis (TGA): Temperature (stability %) 28° C.
(Temp. and & decomposition) (100.0%), 100° C. (99.64%), 150° C. (98.88%), 175° C. (95.35%), 180° C. (86.74%), 200° C. (60.38%), 250° C. (45.03%).

Figure 14:
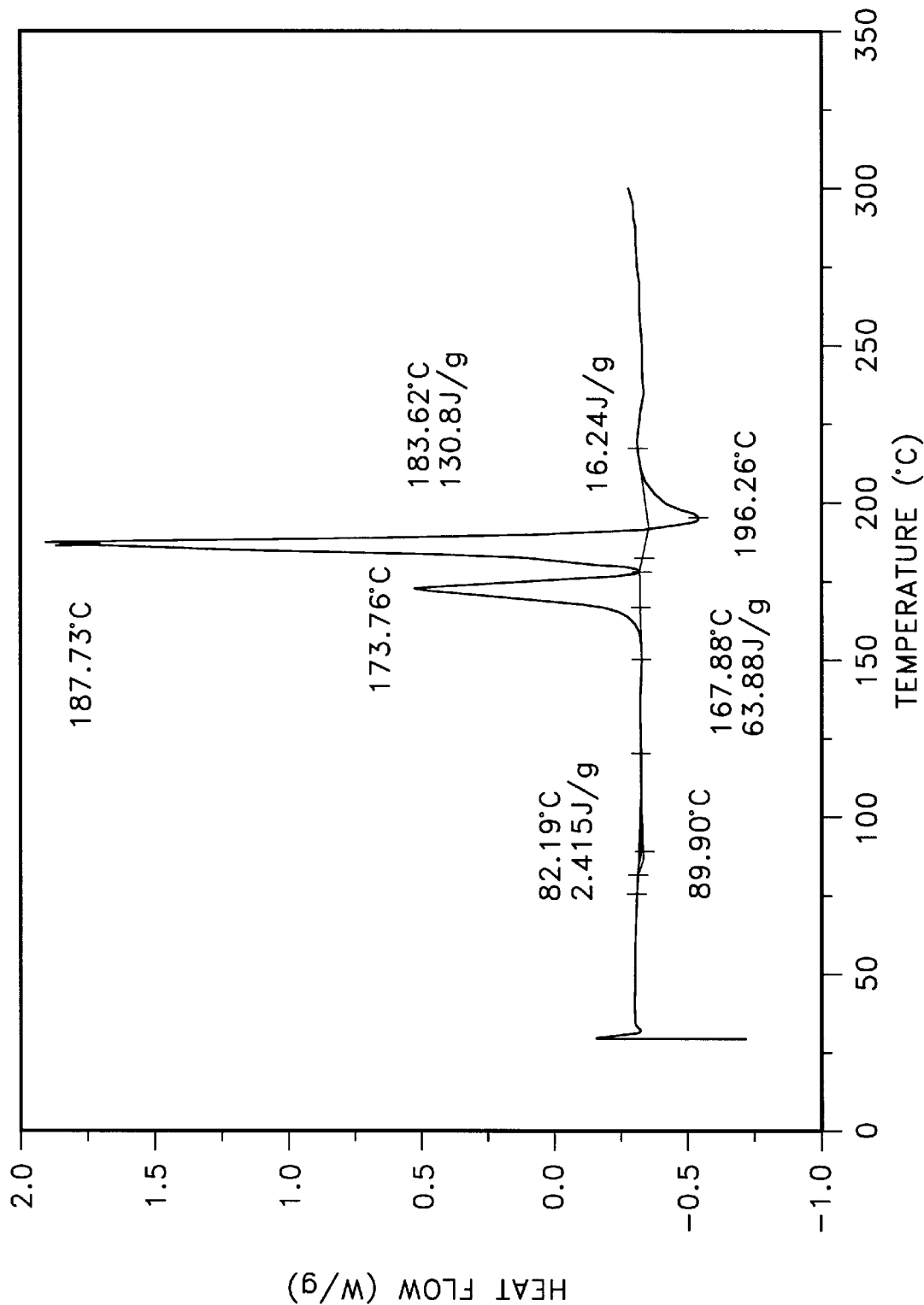
FIG. 14 is a DSC study of 2", 3"-dibromocephalomannine obtained from this invention.

FIG. 14
Differential Scanning Calorimetry (DSC): 173.76° C., 187.73° C.

---

As demonstrated from the following analysis, bromination of the crude paclitaxel mixture shows surprisingly high selectivity for the 2", 3", positions of the unsaturated side chain of cephalomannine, while leaving paclitaxel untouched.

The fractions from #26 to #68 which had a single spot in TLC ($R_f$ 0.49, the same as the authentic sample of paclitaxel) and a single peak in the HPLC, were combined, concentrated and dried, (40° C., high vacuum 1 mm to 2 mm) to yield 6.10 g of a white solid. This material was crystallized from 60 mL of a mixture of acetone/hexane mixture (50:50), filtered, washed with the same ratio of cooled solvents and dried under high vacuum at 40° C. (24 hrs.) to obtain 4.84 g (92%) of a white crystalline solid identified by comparison to an authentic sample as paclitaxel.

Analysis is as follows:

m.p.: 214°–216° C.

$R_f$: 0.49 (in the presence of the authentic sample)

Silica gel 60 $F_{254}$ plate (merck #5554)

Solvent system: acetone/$CH_2Cl_2$ (20:80)

Spary Reagent: Vanillin/Sulfuric Acid in Methanol

Elemental Analysis:

| $C_{47}H_{51}O_{14}N$: | % C | % H | % N |
|---|---|---|---|
| Calculated | 66.11 | 6.02 | 1.64 |
| Found | 65.97 | 5.89 | 1.63 |

$[α]_D^{25}$ = −51.104°(c 0.33, MeOH)

| UV Spectrum in CH₃OH: | | |
|---|---|---|
| ($λ_{max}$ in nm, (ε)) | 227.2 | (29824.1) |
| | 208.0 | (26256.3) |
| IR Spectrum (KBr) (cm$^{-1}$) | 3500, 1105, 1070 (tert. & sec. OH) | |
| | 3430, 1650, 1580 (—CONH—) | |
| | 1610, 1520, 780, 710 (monosub. aromatic rings) | |
| | 2950, 2910, 1480, 1450, 1370 (—CH₃, —CH₂—, >CH— groups) | |
| | 3020, 1315, 980 (double bond) | |
| | 1725, 1270 (aromatic esters) | |
| | 1710, 1240 (>C=O) | |
| | 850 (epoxy rings) | |
| ¹H NMR Spectrum: | 1.88 (S, 10H, C-1); 5.66 (d, 1H, C-2); 3.82 (dd, 1H, C-3); | |
| (300 MHz; CDCl₃) | 2.38 (S, 3H, CH₃COO at C-4); 4.94 (dd, 1H, C-5); | |
| (ppm) | 1.88 (ddd, 1H, C-6); 2.48 (ddd, 1H, C-6); 2.53 (d, 10H, C-7); | |
| | 4.38 (dd, 1H, C-7); 6.27 (S, 1H, C-10); | |
| | 2.23 (S, 3H, CH₃COO at C-10); 6.20 (qt, 1H, C-13); | |
| | 2.27 (ddd, 1H, C-14); 2.33 (dd, 1H, C-14); 1.13 (S, 3H, C-19); | |
| | 1.23 (S, 3H, C-18); 1.78 (S, 3H, C-18); 1.68 (S, 3H, C-19); | |
| | 4.20 (dd, 1H, C-20); 4.30 (S, 1H, C-20); 3.77 (S, 1H, C-2'); | |
| | 4.78 (ddd, 1H, C-2'), 5.20 (ddd, 1H, C-3'), 7.10 (d, 1H, N-1); | |
| | 7.30–7.53 (m, 10H, p-&m-protons at aromatic rings A₁, B₁, | |
| | & C₁); 7.64 (t, 1H, A₁-p); 7.72 (dd, 2H, C₁-o); 8.11 (dd, 2H, A₁-o). | |
| ¹³C NMR Spectrum | 79.1 (C-1); 75.1 (C-2); 45.8 (C-3); 81.2 (C-4); 84.4 (C-5); | |
| (300 MHz, CDCl₃) | 35.6 (C-6); 72.1 (C-7); 56.7 (C-8); 203.6 (C-9); 75.6 (C-10); | |
| (ppm) | 133.3 (C-11); 141.9 (C12); 72.3 (C-13); 35.7 (C-14); 43.2 (C- | |
| | 15); 21.8 (C-16); 26.9 (C-17); 14.7 (C-18); 9.5 (C-19); | |
| | 76.5 (C-20); 73.3 (C-2'); 55.1 (C-3'); 20.7 (CH₃CO)at C-10; | |
| | 22.6 (CH₃CO at C-4); 170.3 (CH₃CO at C-10); | |
| | 171.1 (CH₃CO at C-4); 167.0 (ArCO-A₁); 167.0 (ArCO-C₁); | |

-continued

| | |
|---|---|
| | 172.7 (PhISCO—); 129.3 (aC-$A_1$); 133.8 (aC-$B_1$); 138.1 (aC-$C_1$); 130.3 (o-C, $A_1$); 127.0 (o-C, $B_1$); 127.0 (o-C, $C_1$); 128.7 (m-C, $A_1$); 128.6 (m-C, $B_1$); 129.0 (m-C, $C_1$); 133.6 (p-C, $A_1$); 131.9 (p-C, $B_1$); 128.3 (p-C, $C_1$). |
| EIMS: $[M]^+$ = 853 (m/z, the main fragments) | 568$[T]^+$; 550$[T-H_2O]^+$; 508$[T-AcOH]^+$; 490$[T-AcOH—H_2O]^+$; 448$[T-2AcOH]^+$ or $[T-BzOH]^+$; 386$[T-AcOH—BzOH]^+$; 326$[T-BzOH-2AcOH]^+$; 308$[326-H_2O]^+$; 286$[M-T]^+$ or $[S]^+$; 280; 268 $[S—O]^+$; 240$[S—O—CO]^+$; 210$[S—O—CO—HCOH]^+$; 122$[BzOH]^+$; 105$[Bz]^+$; 91$[C_7H_7]^+$; 77$[C_6H_5]^+$; 51; 43 $[Ac]^+$. |
| DC/MS: $[M + H]^+$ = 854 (m/z; the main fragments) | 569; 551; 509; 492; 449; 387; 327; 311; 287; 269; 240; 224; 222; 210; 165; 149; 123; 105; 92; 71. |
| FAB MS:(positive ion mode): (m/z; the main fragments) | 892$[M + K]^+$; 876$[M + Na]^+$; 854$[M + H]^+$; 569; 551; 523; 509; 495; 369; 327; 286; 240; 210; 177; 155; 149; 119; 105; 85; 69. |
| FAB MS: (negative ion mode): | 852 - $[M - H]^-$ |
| HPLC: | |
| Column: | µBondapak Phenyl |
| Solvent System: | $CH_3CN:CH_3OH:H_2O$-132:20:48 |
| Flow Rate: | 1 mL/min |
| Detector: | Waters 490 uv at 227 nm |
| Injection volume: | 20 µL |
| TGA: | 50° C. (100.0%), 205° C. (99.86%), 215° C. (99.10%), 220° C. (92.19%), 250° C. (56.66%), 275° C. (45.92%). |
| DSC: | 210° C. |
| Water content (% $H_2O$): | 0.90%(Karl Fischer) |

EXAMPLE 4

In Vitro Studies Showing Antitumor Efficacy of Dibromocephalomannine which Correlate to Known In Vivo Paclitaxel Antitumor Efficacy As is known, paclitaxel shows highly desirable antitumor efficacy, and acts in a unique way by binding to microtubules to stabilize them from depolymerization, or inducing abnormal polymerization of tubulin, resulting in the disruption of cell mitosis, and cancer cell proliferation. The mechanism of action of paclitaxel, pharmacology etc. is described in detail, for example, in Rowinsky et al., *Taxol: A Novel Investigational Antimicrotuble Agent*, 2. Natl. Cancer Inst., 82:1247 (1990).

In accordance with the present invention, the novel 2", 3"-dibromocephalomannine compound also shows strong paclitaxel-like antitumor efficacy, which provides a valuable addition to the arsenal of antitumor therapeutic agents.

The following in vitro studies conducted by the National Cancer Institute's Developmental Therapeutics Program demonstrate the strong antitumor efficacy of dibromocephalomannine which is similar to that of paclitaxel and superior to that of Taxotere.

The Developmental Therapeutics Program provides as a service to the public an in vitro anticancer drug discovery screen using a panel of sixty different human tumor cell lines over which candidate drugs are tested at defined ranges of concentrations. See Boyd et al., Drug Development Research 34:91–109 (1995), the entirety of which is incorporated herein by reference.

As discussed in Boyd et al., the screen is designed and operated in such a manner that both relative and absolute sensitivities of each of the cell lines comprising the screen are reproducible to the degree that a characteristic profile ("fingerprint") of a respective cell lines' response to a drug candidate can be generated.

Recent studies of the in vivo counterpart of the NCI in vitro screen have indicated the in vitro screen to be an effective selector of compounds with in vivo anticancer efficacy. See Grever et al., Proc. Am. Assoc. Cancer Res. 35:369 (1994).

Figure 15C:
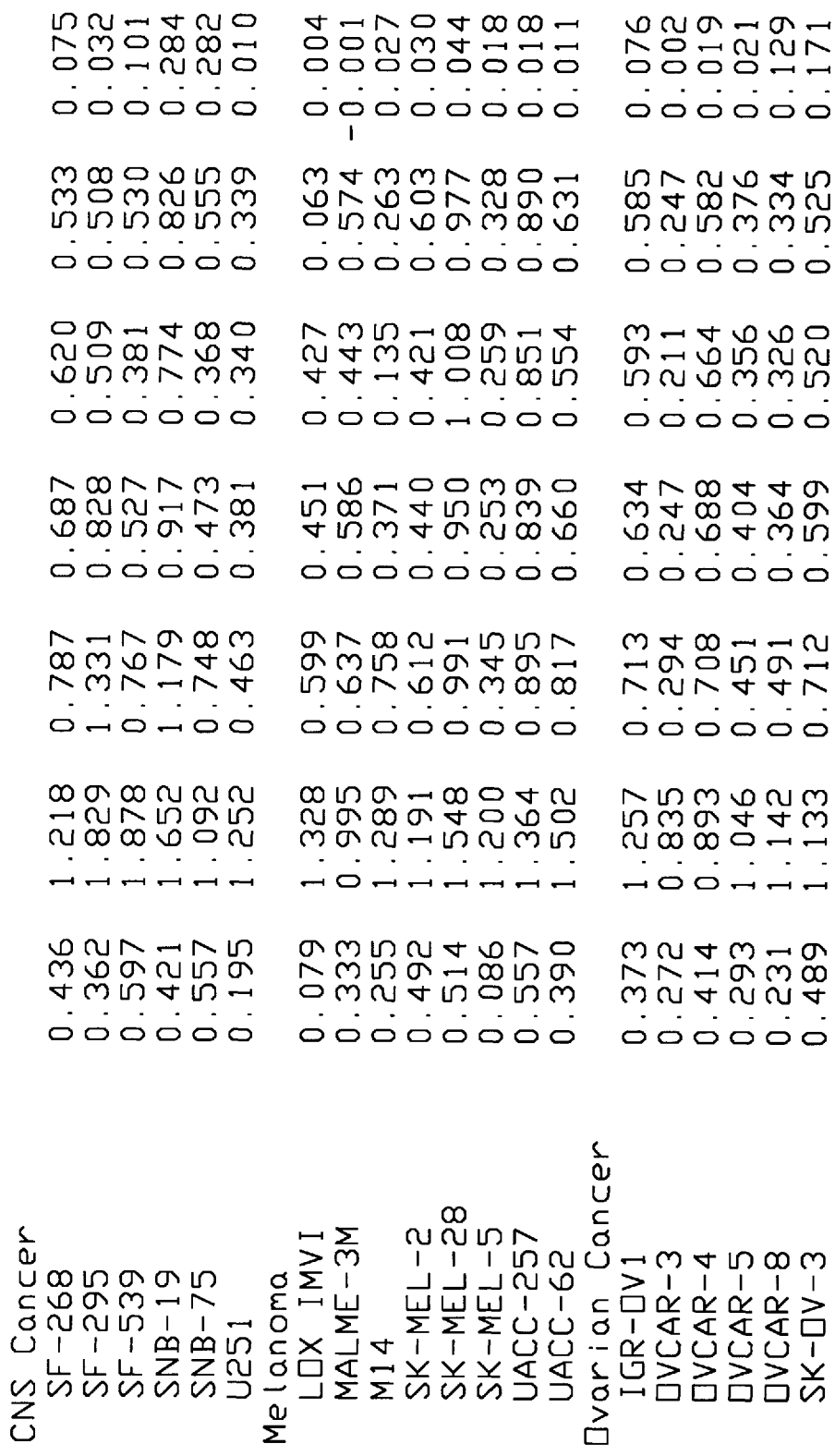
FIG. 15 represents a data sheet of in vitro testing results of 2", 3"-dibromocephalomannine obtained from this invention in a screen of sixty tumor cell lines.
Figure 16B:
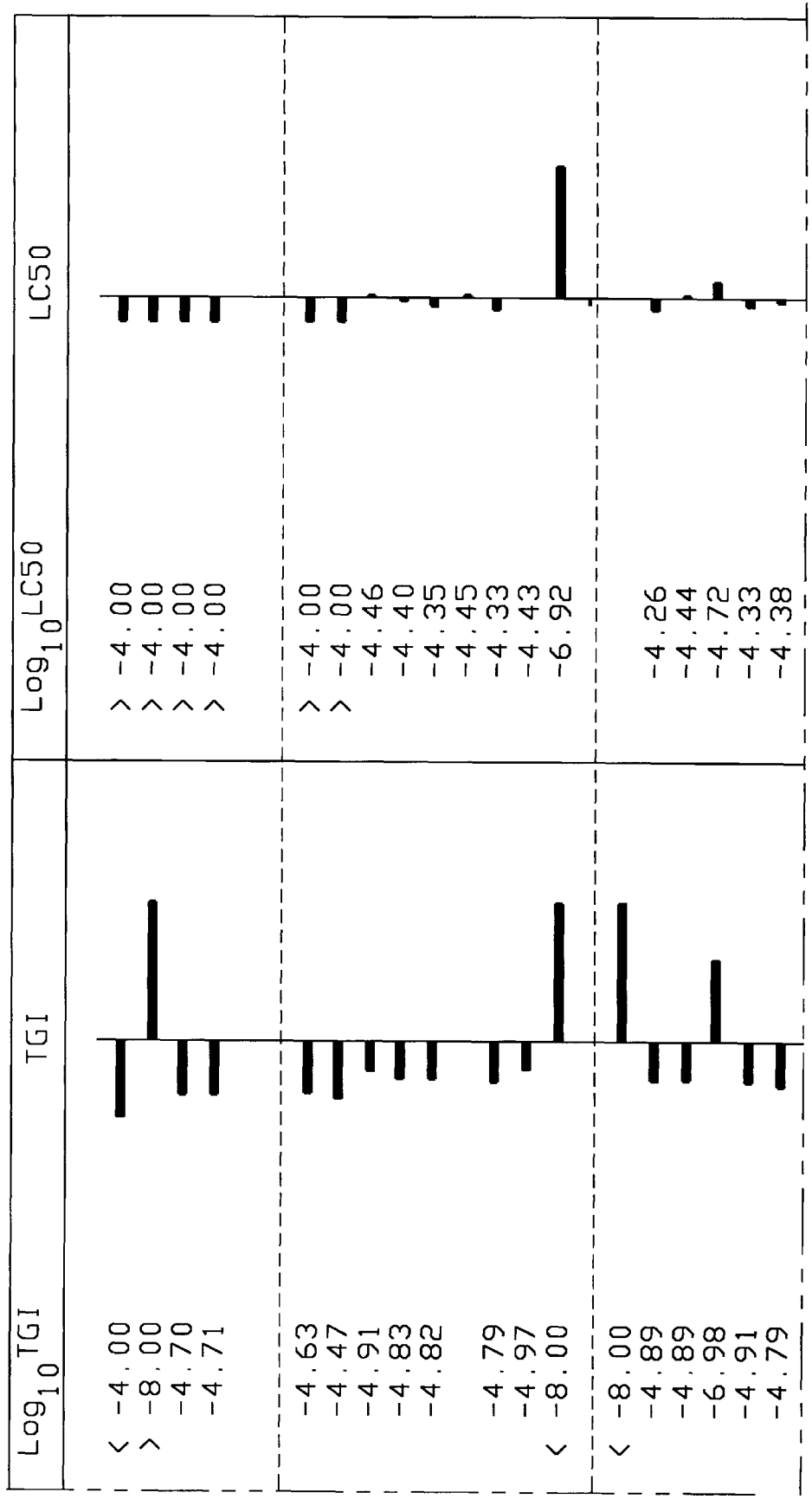
FIG. 16 represent mean graphs of dose response of 2", 3"-dibromocephalomannine obtained from this invention in a screen of sixty tumor cell lines.
Figure 16C:
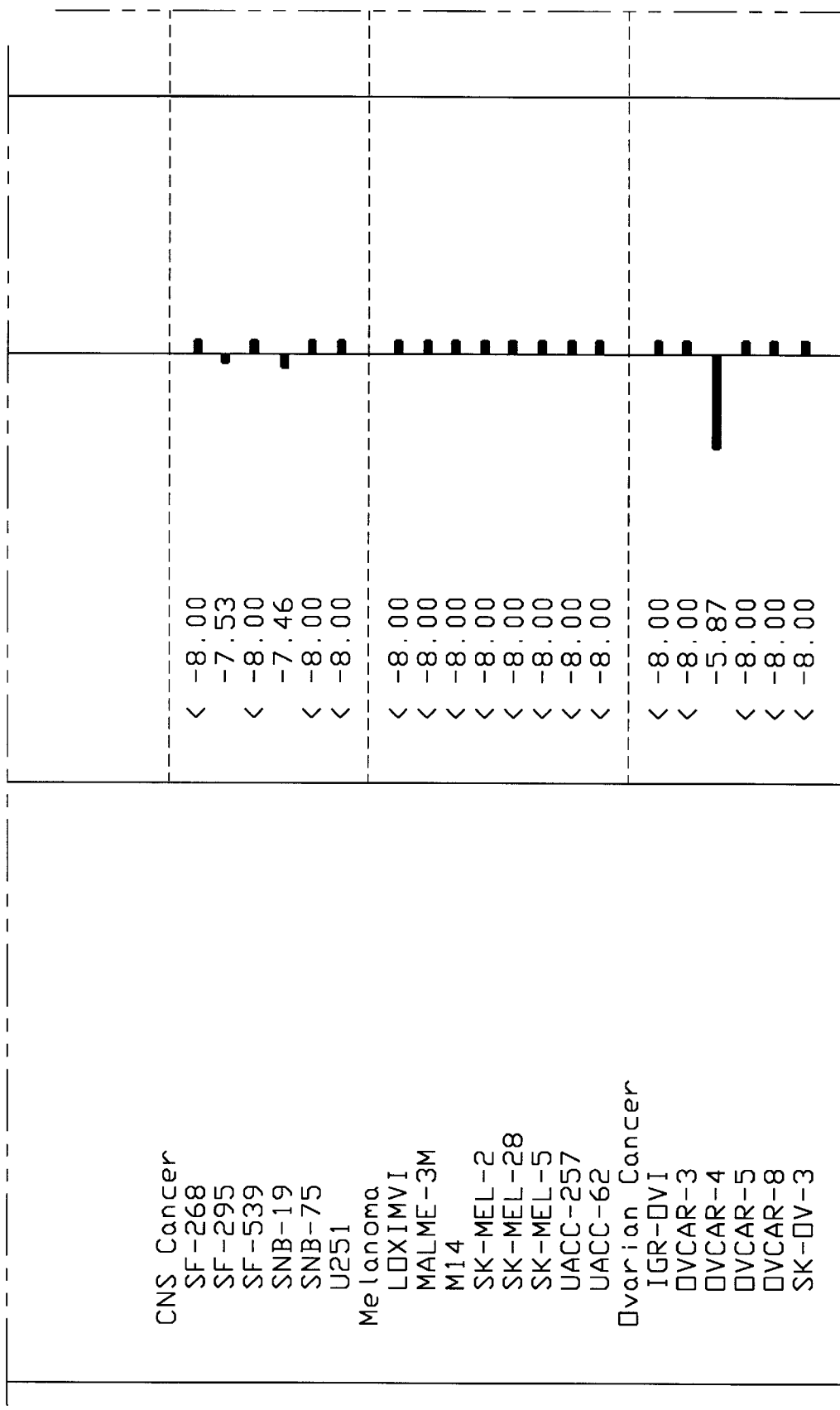
Figure 16D:
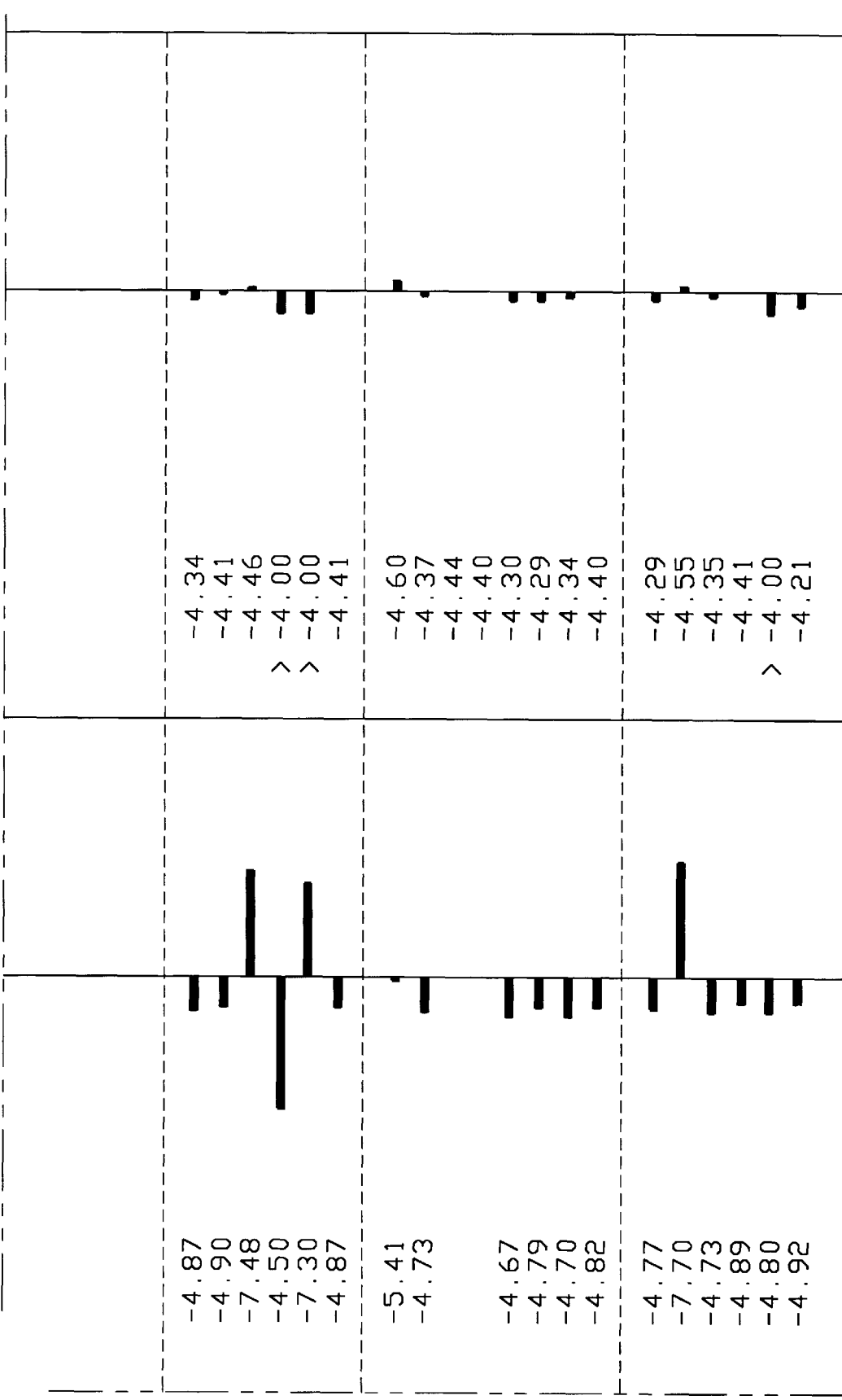
Figure 16E:
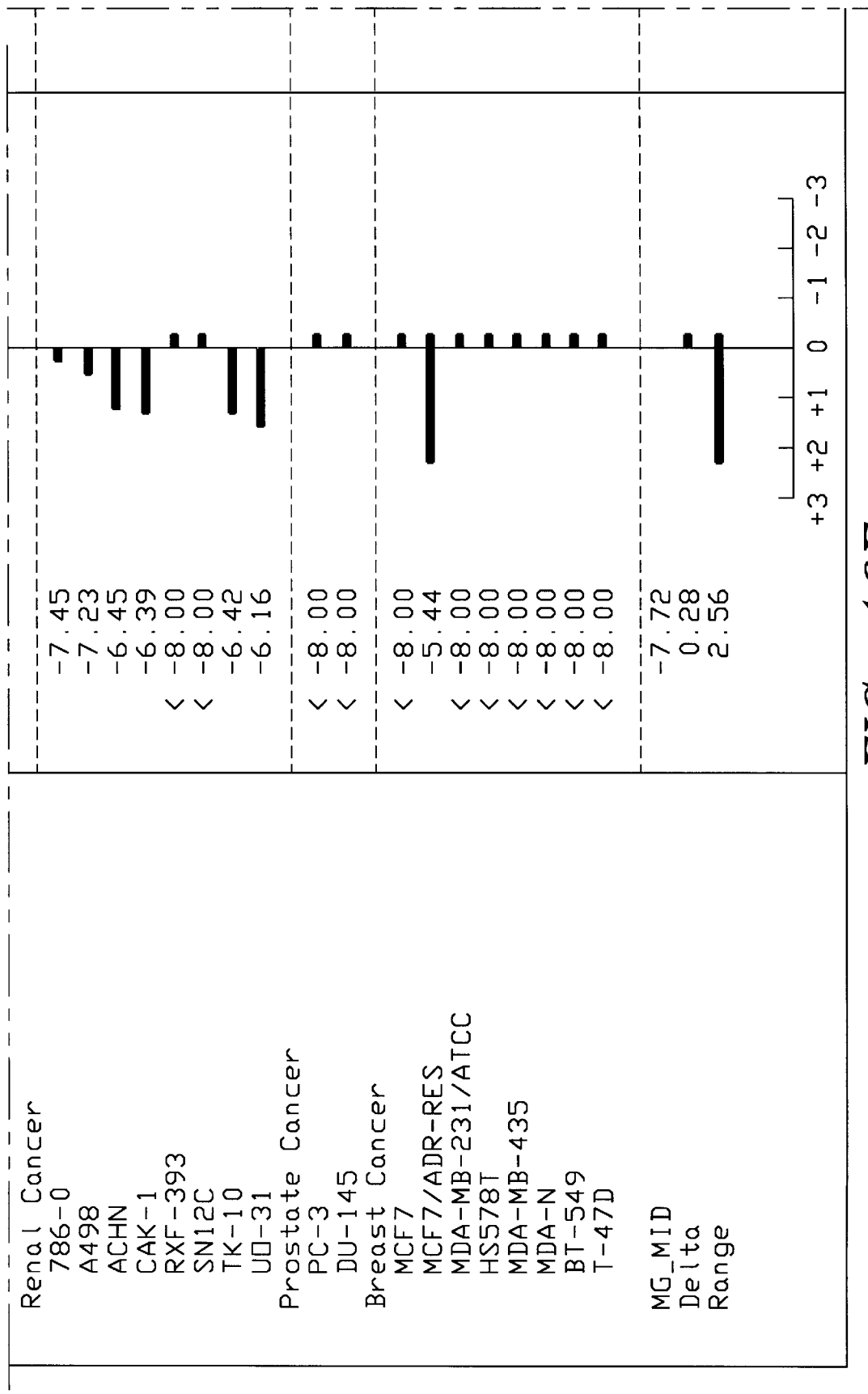
Figure 16F:
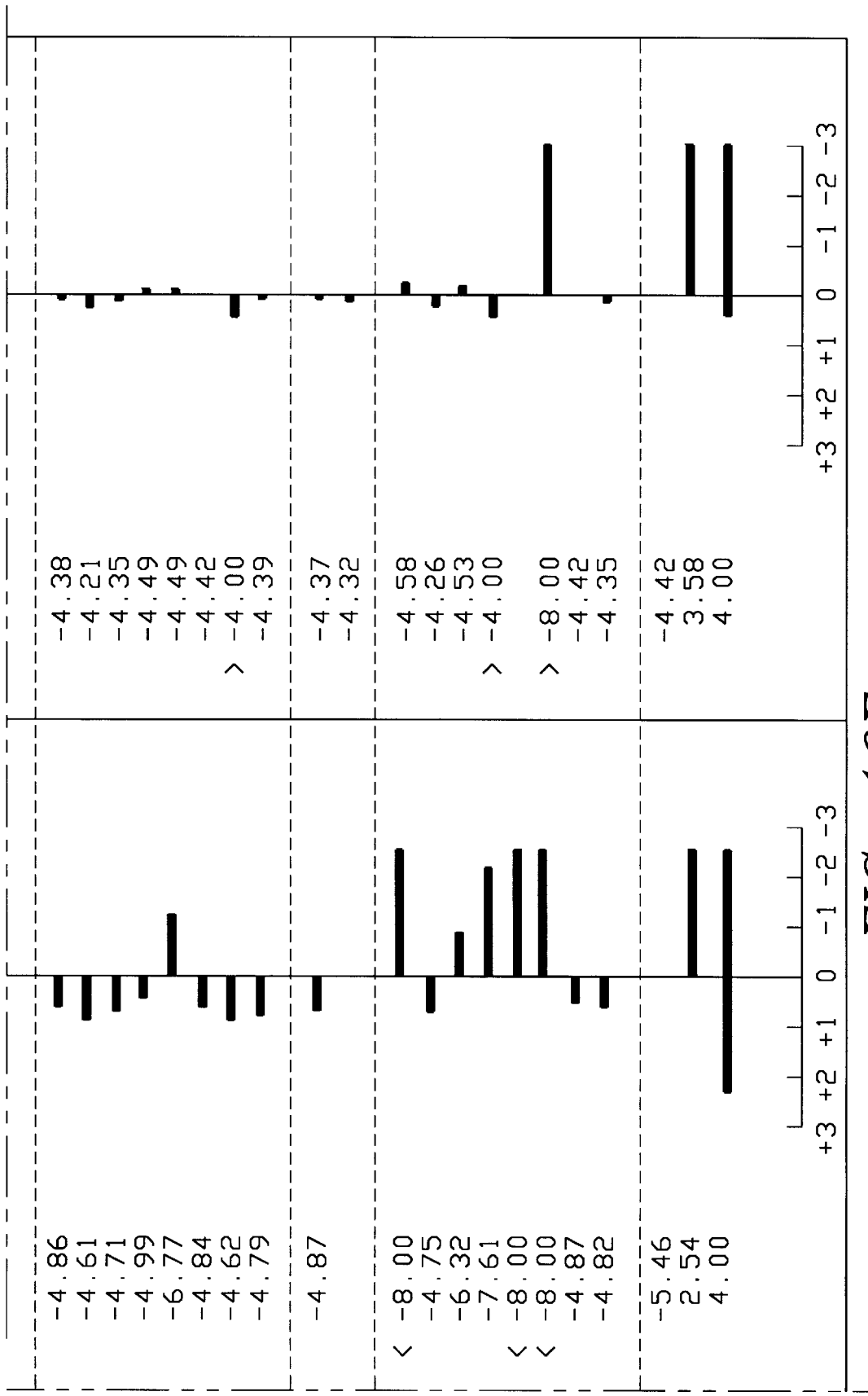
Figure 17A:
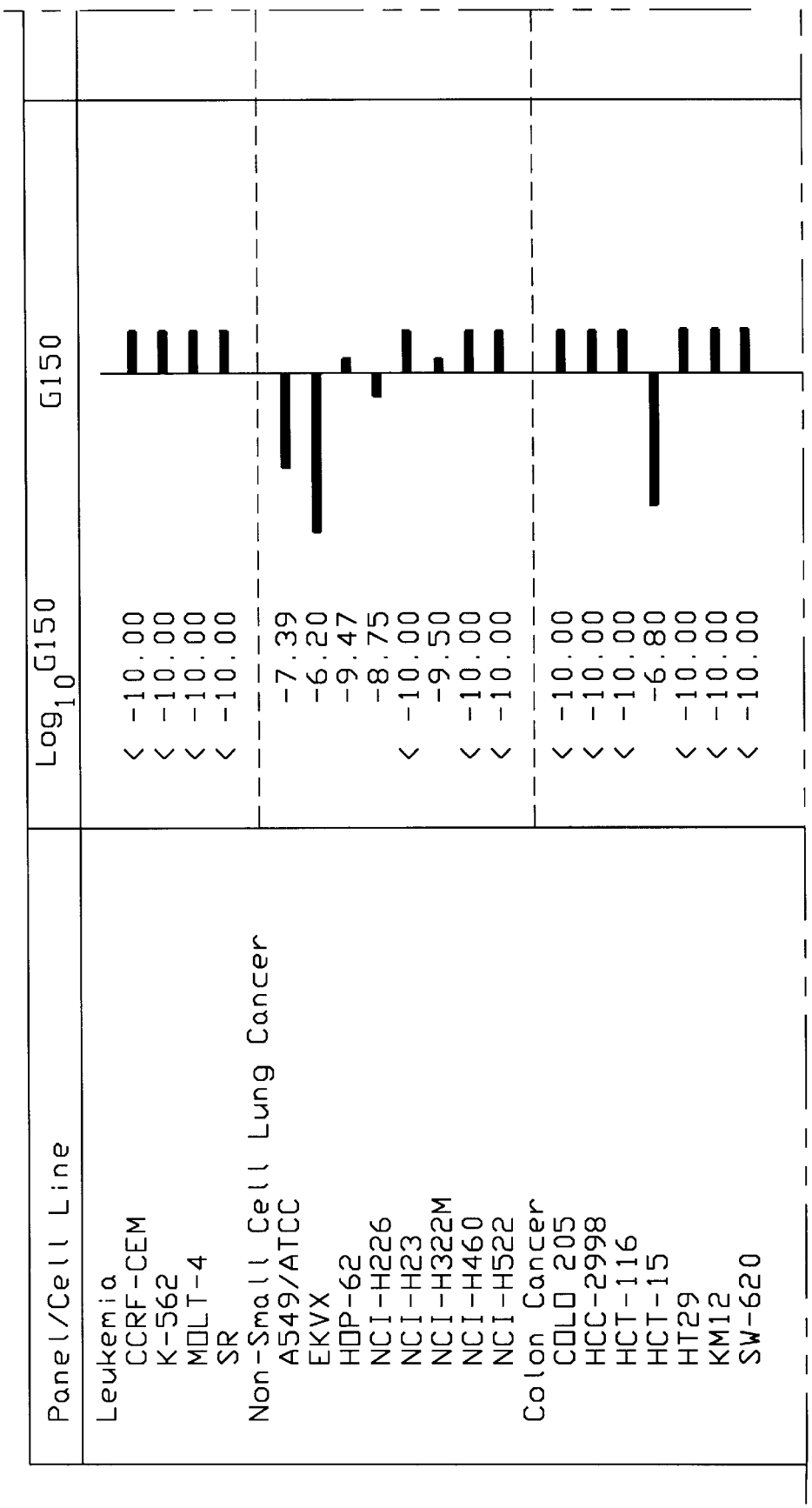
FIG. 17 represent mean graphs of dose response of paclitaxel in a screen of sixty tumor cell lines.
Figure 17B:
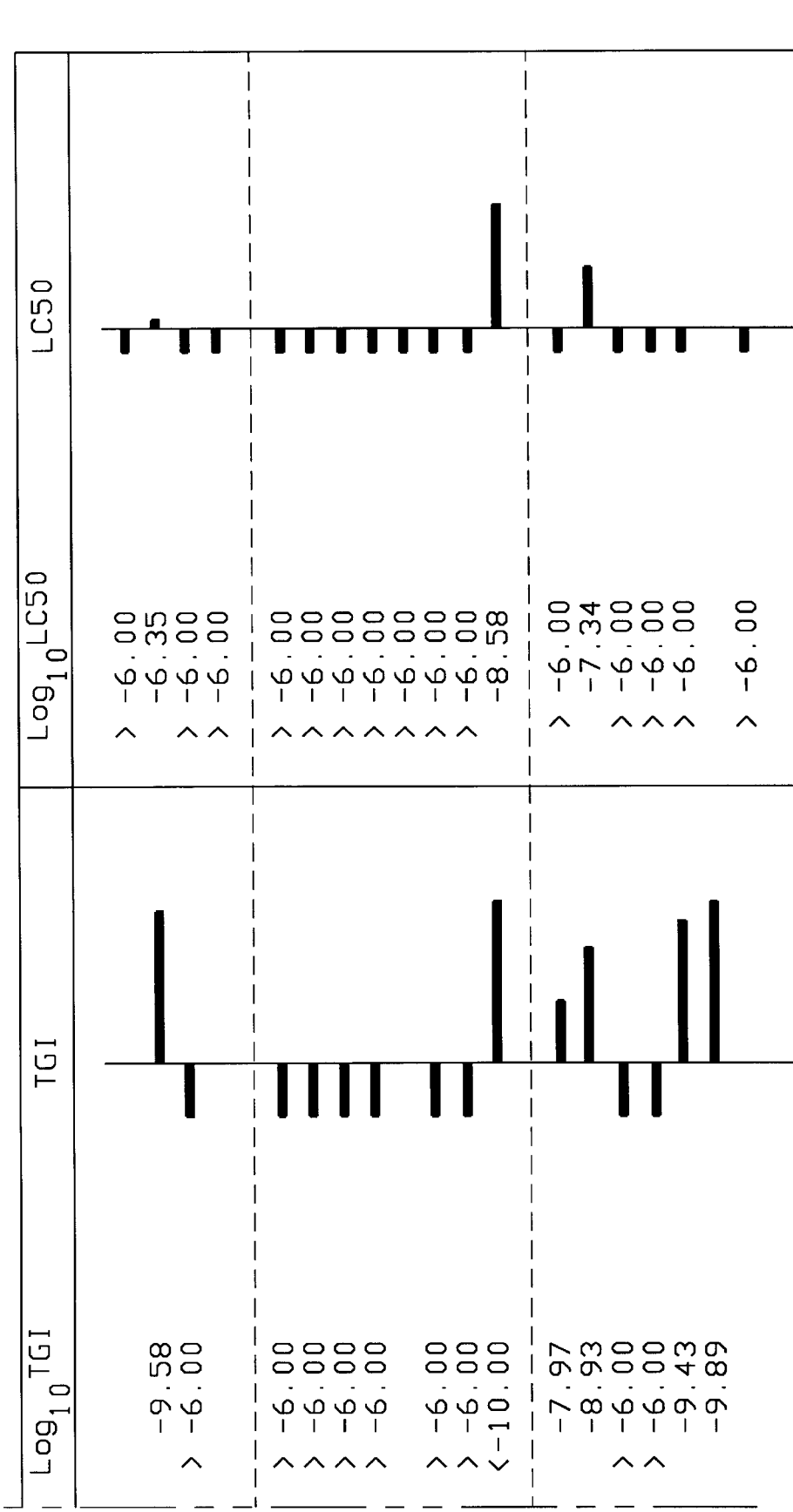
Figure 17C:
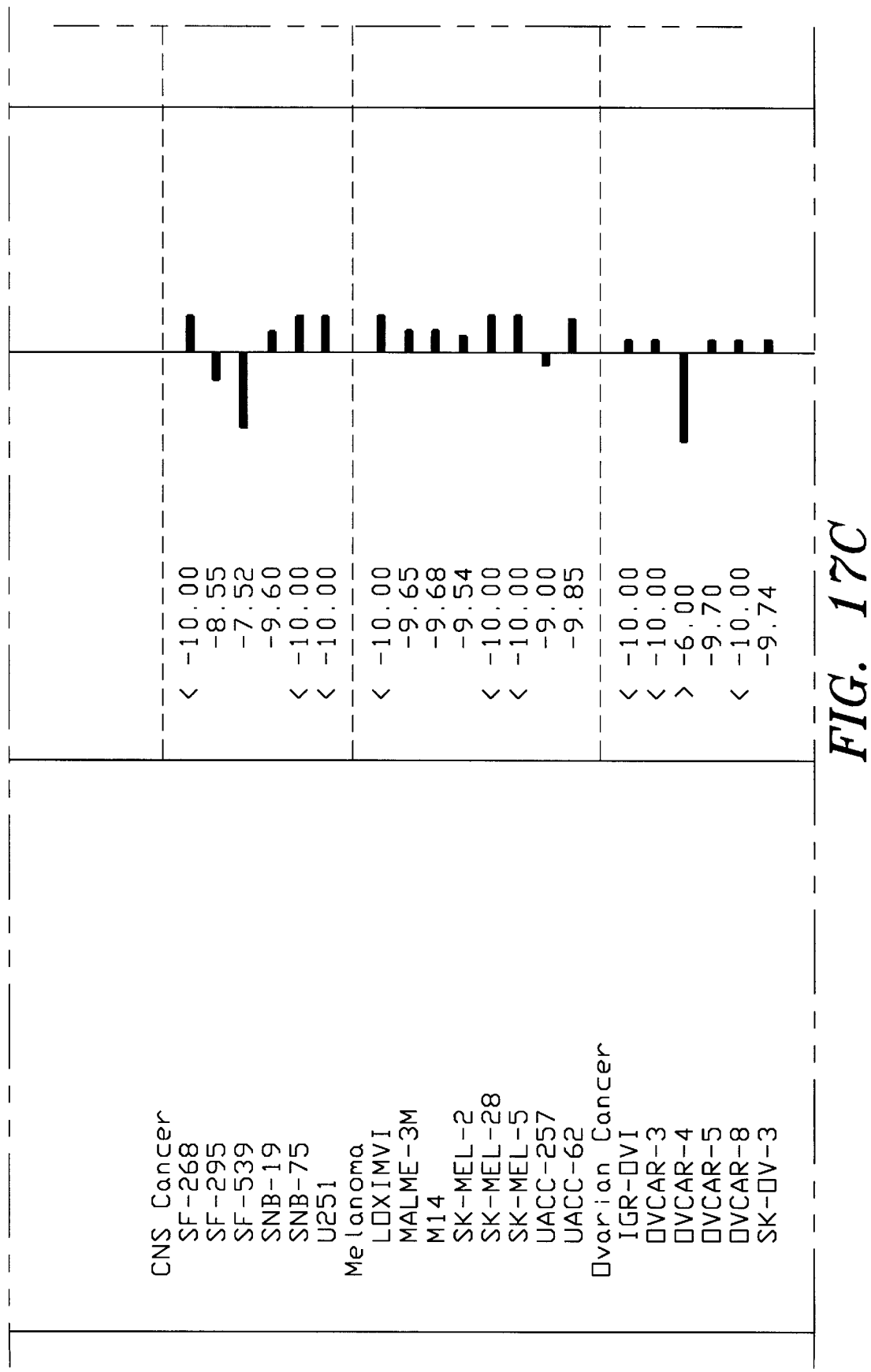
Figure 17D:
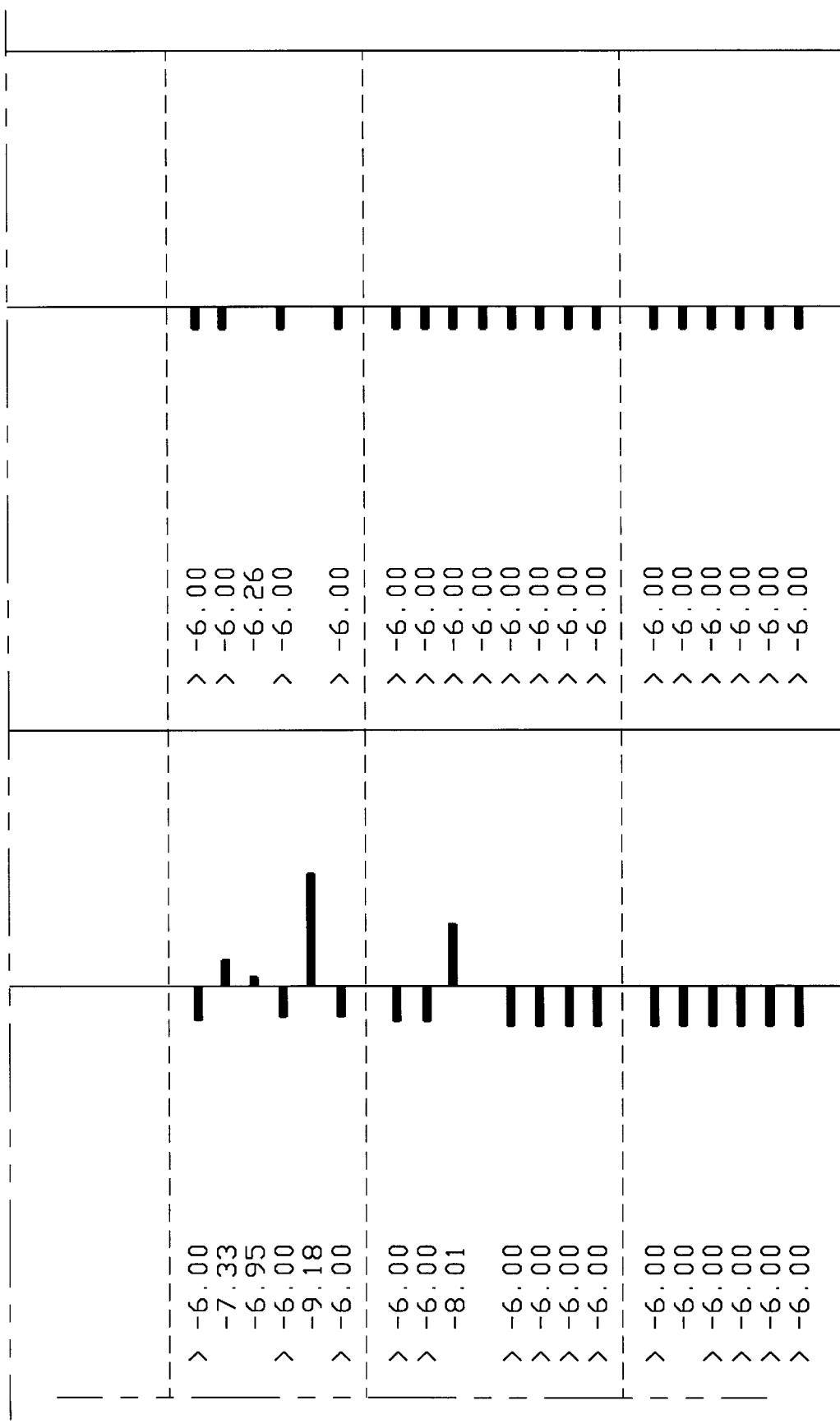
Figure 17E:
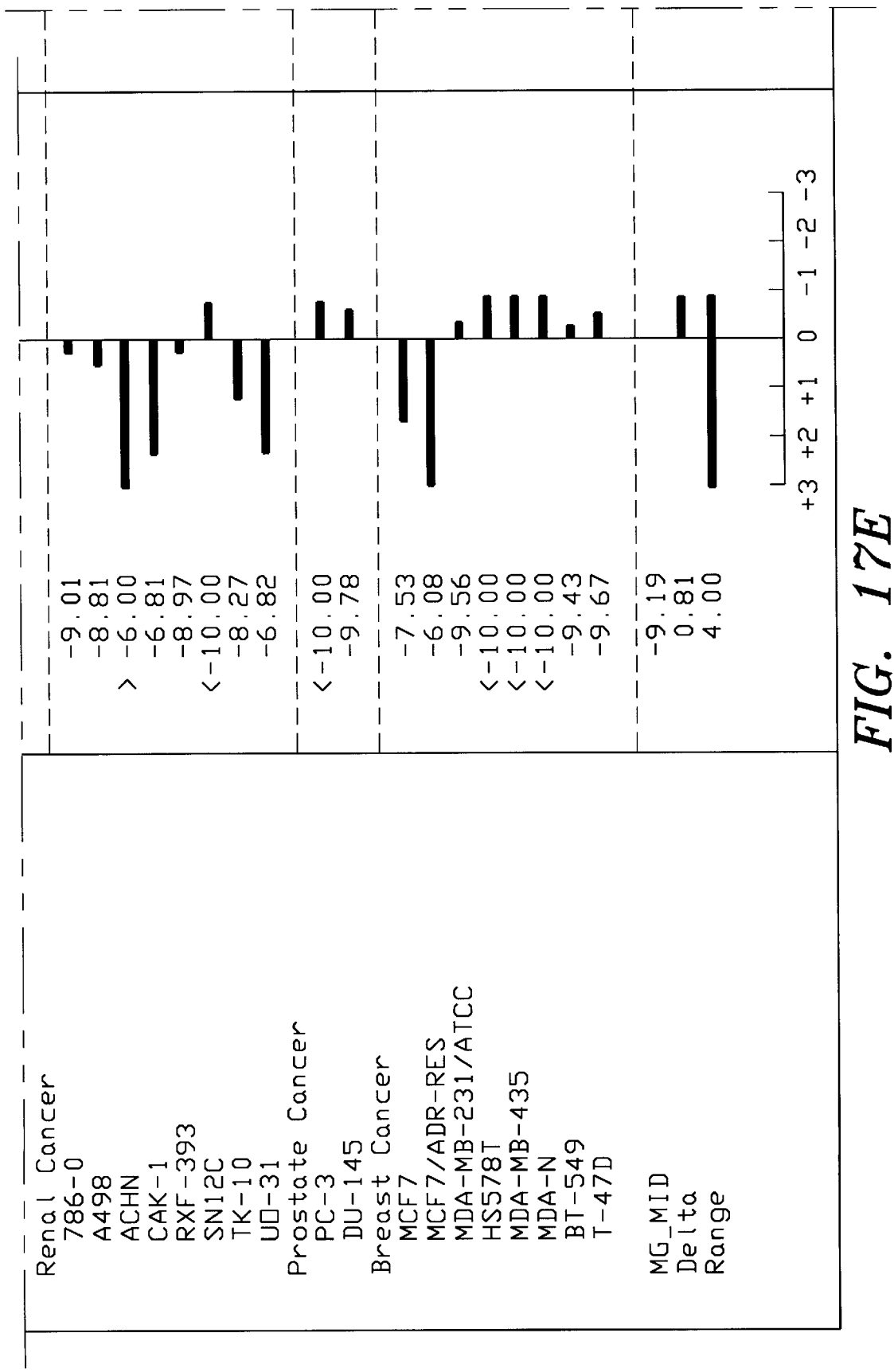
Figure 17F:
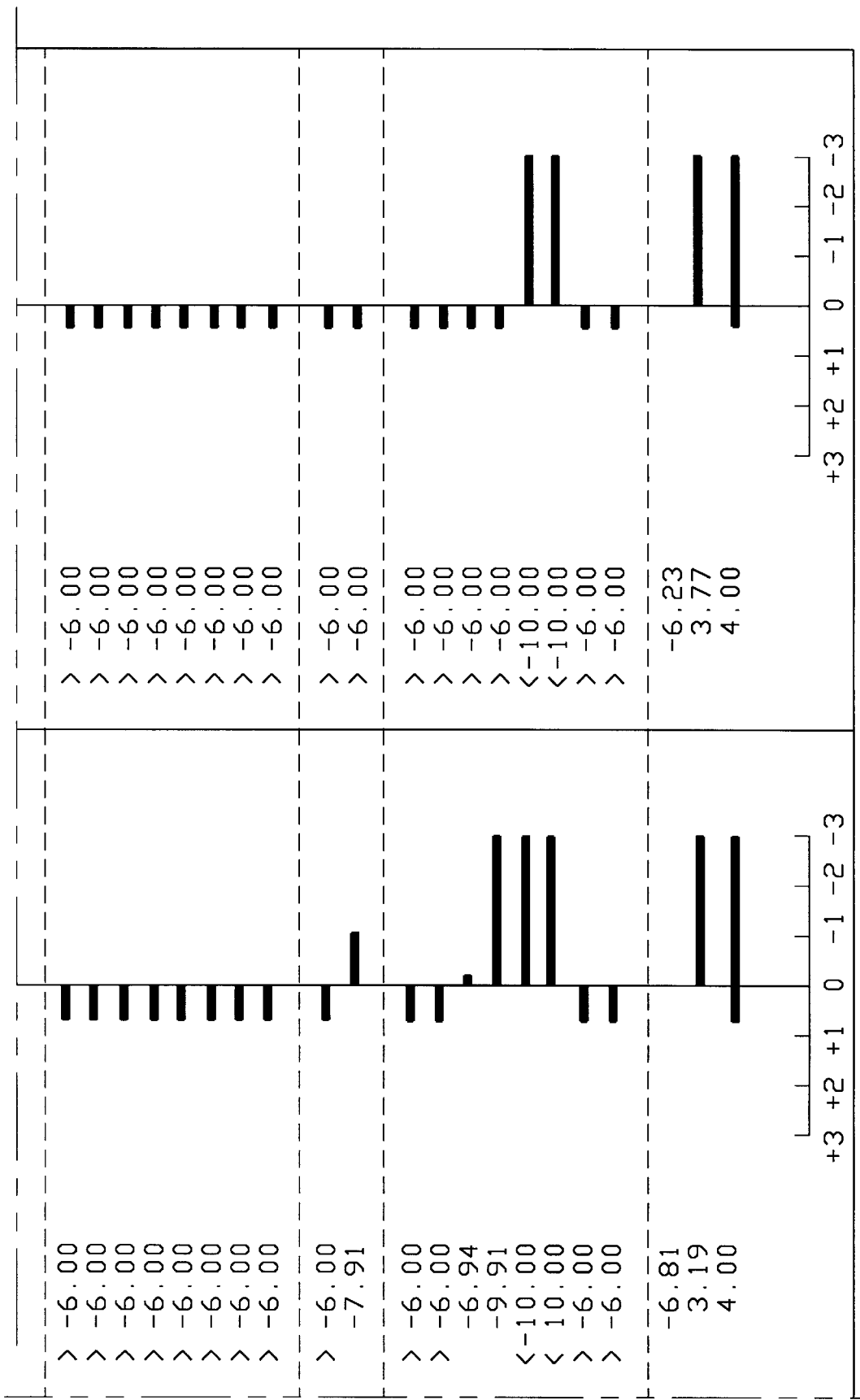
Figure 18B:
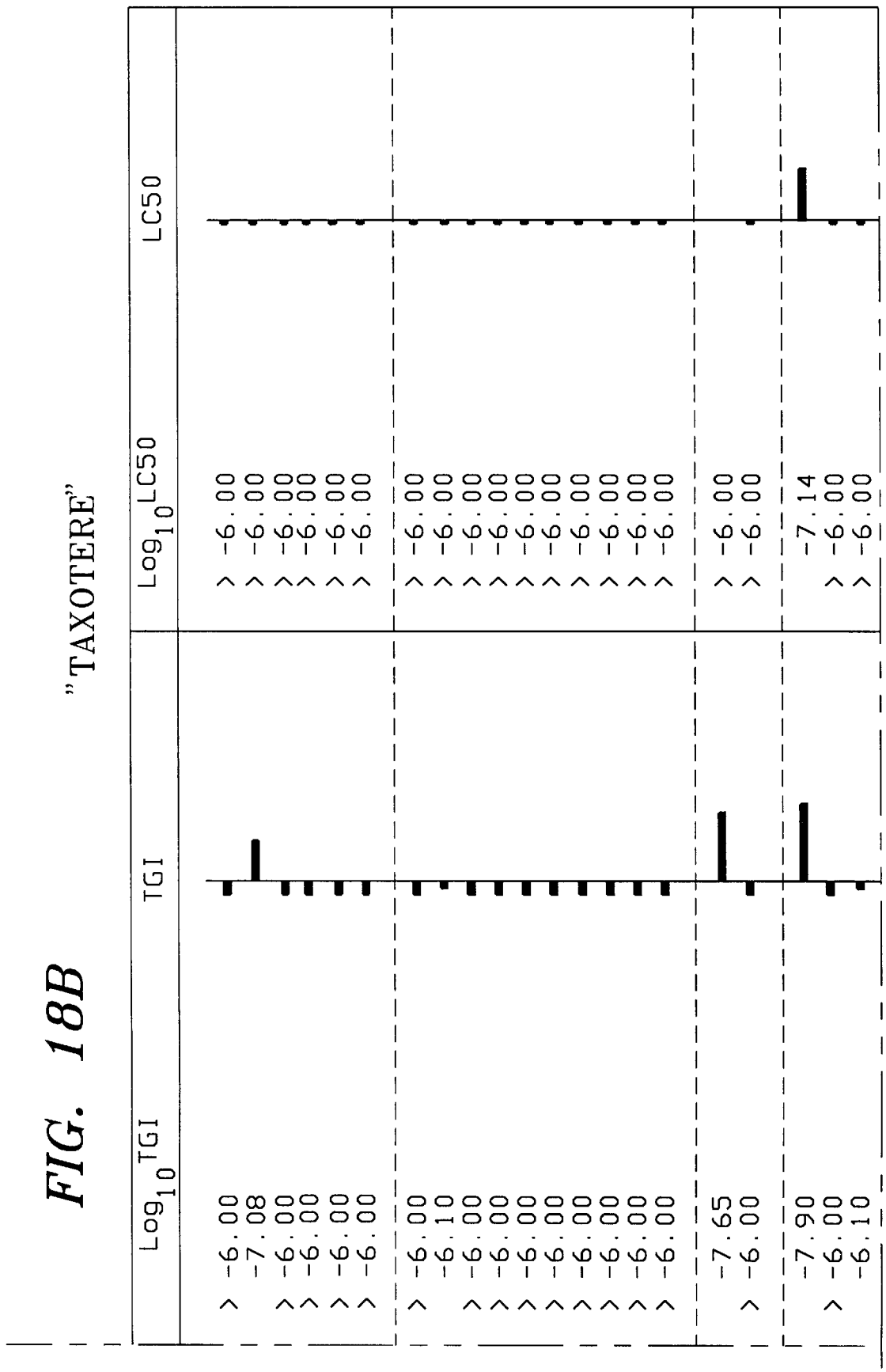
FIG. 18 represent mean graphs of dose response of taxotere in a screen of sixty tumor cell lines.
Figure 18C:
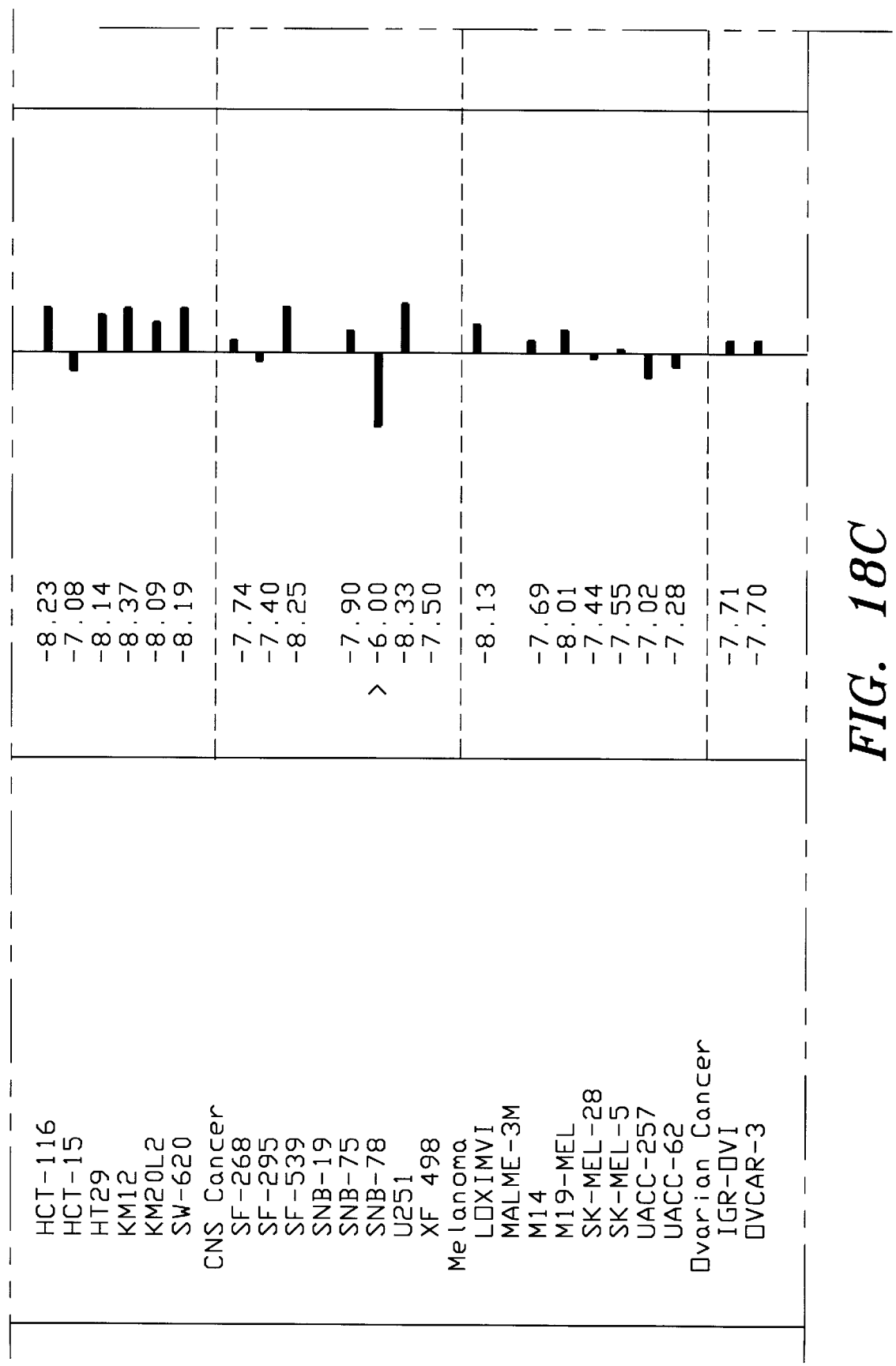
Figure 18D:
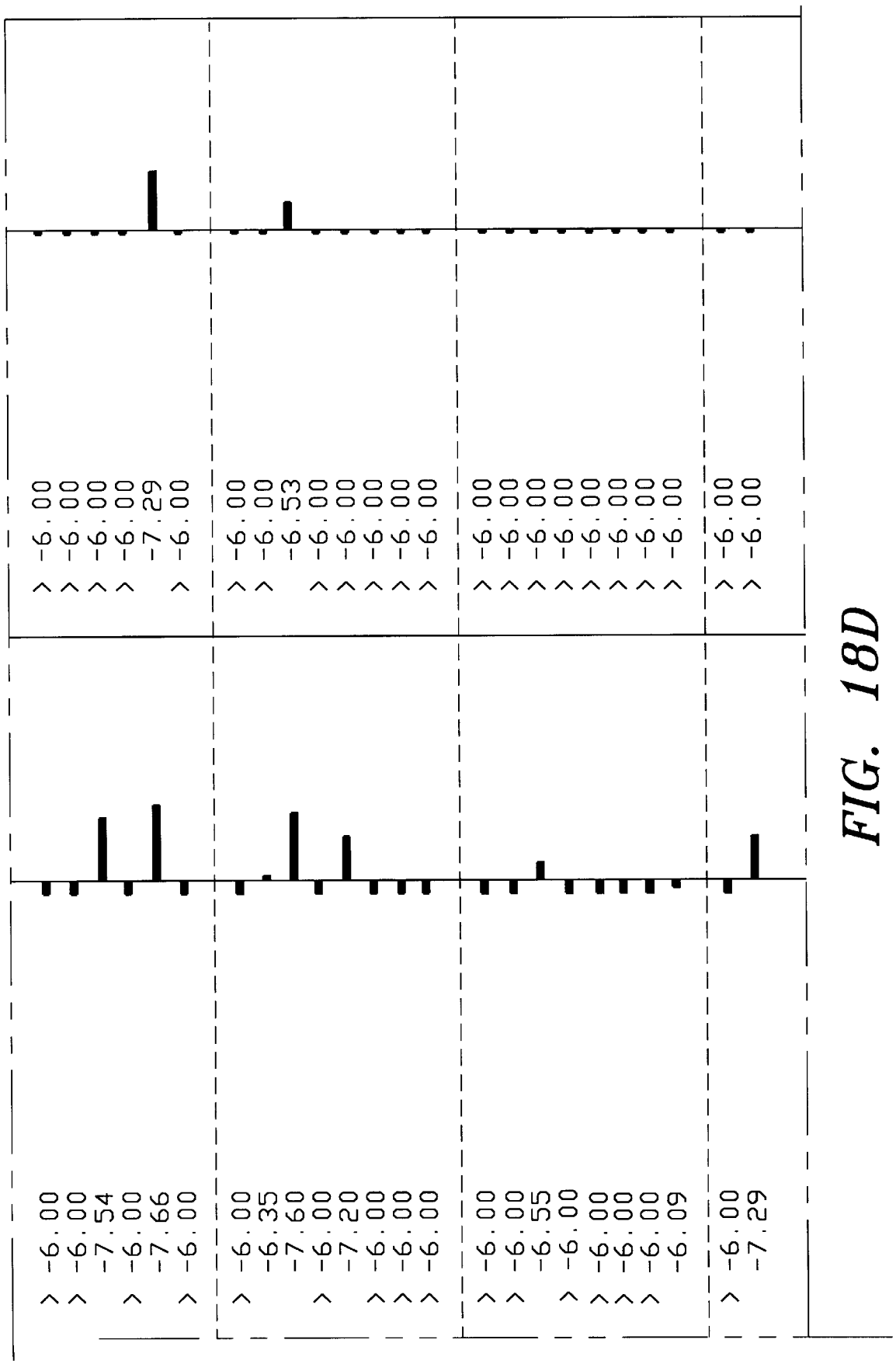
Figure 18E:
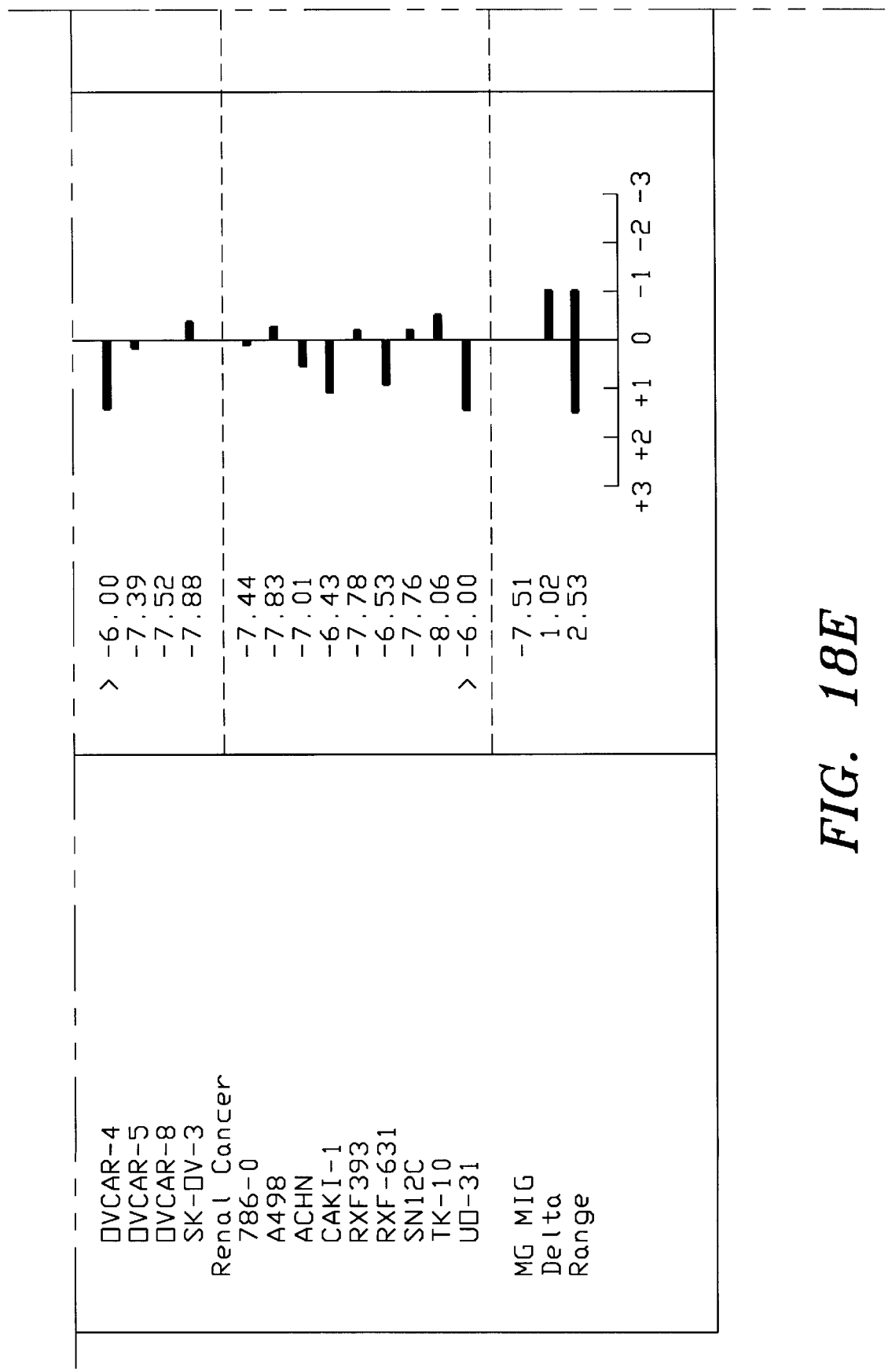
Figure 18F:
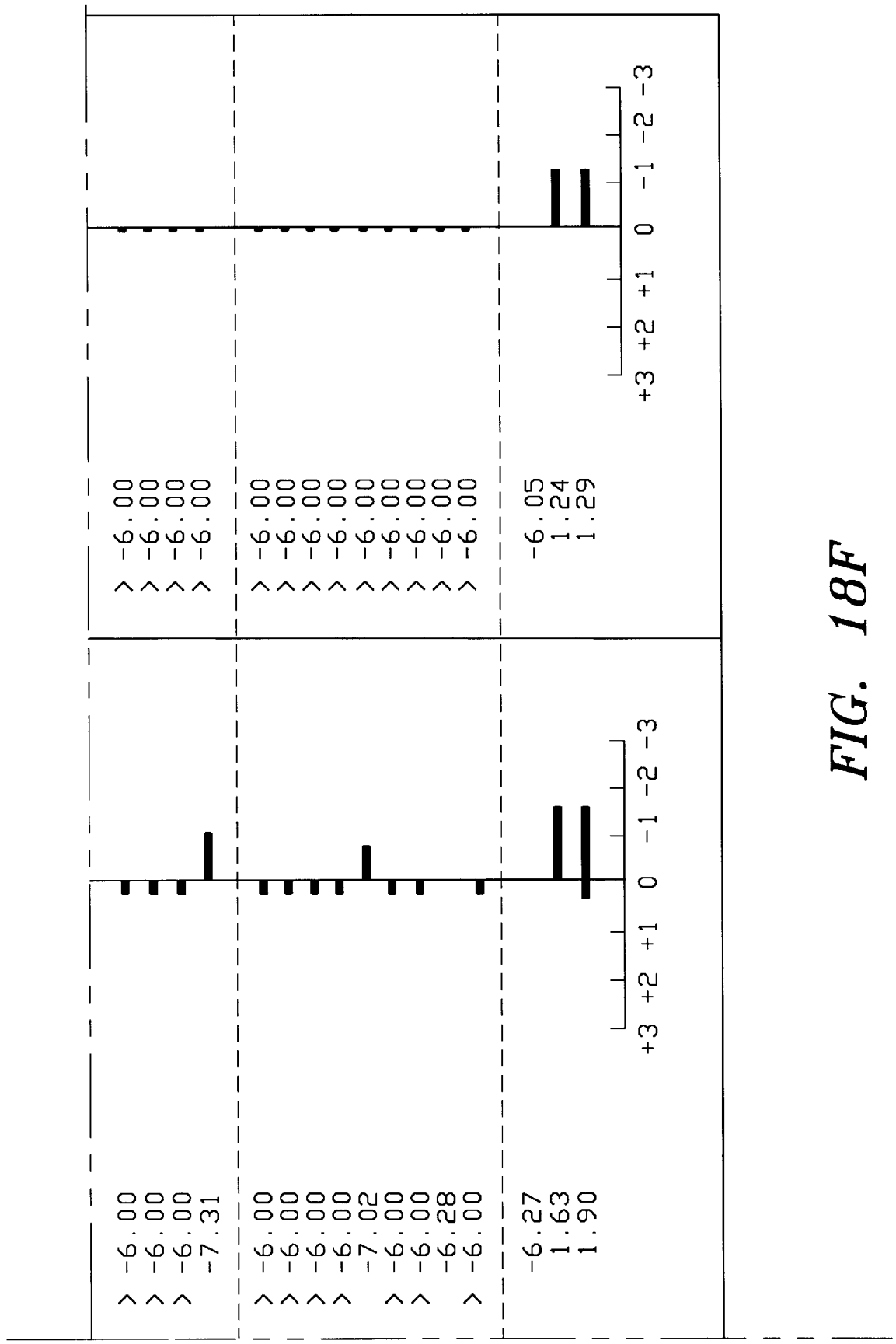
Figure 19A:
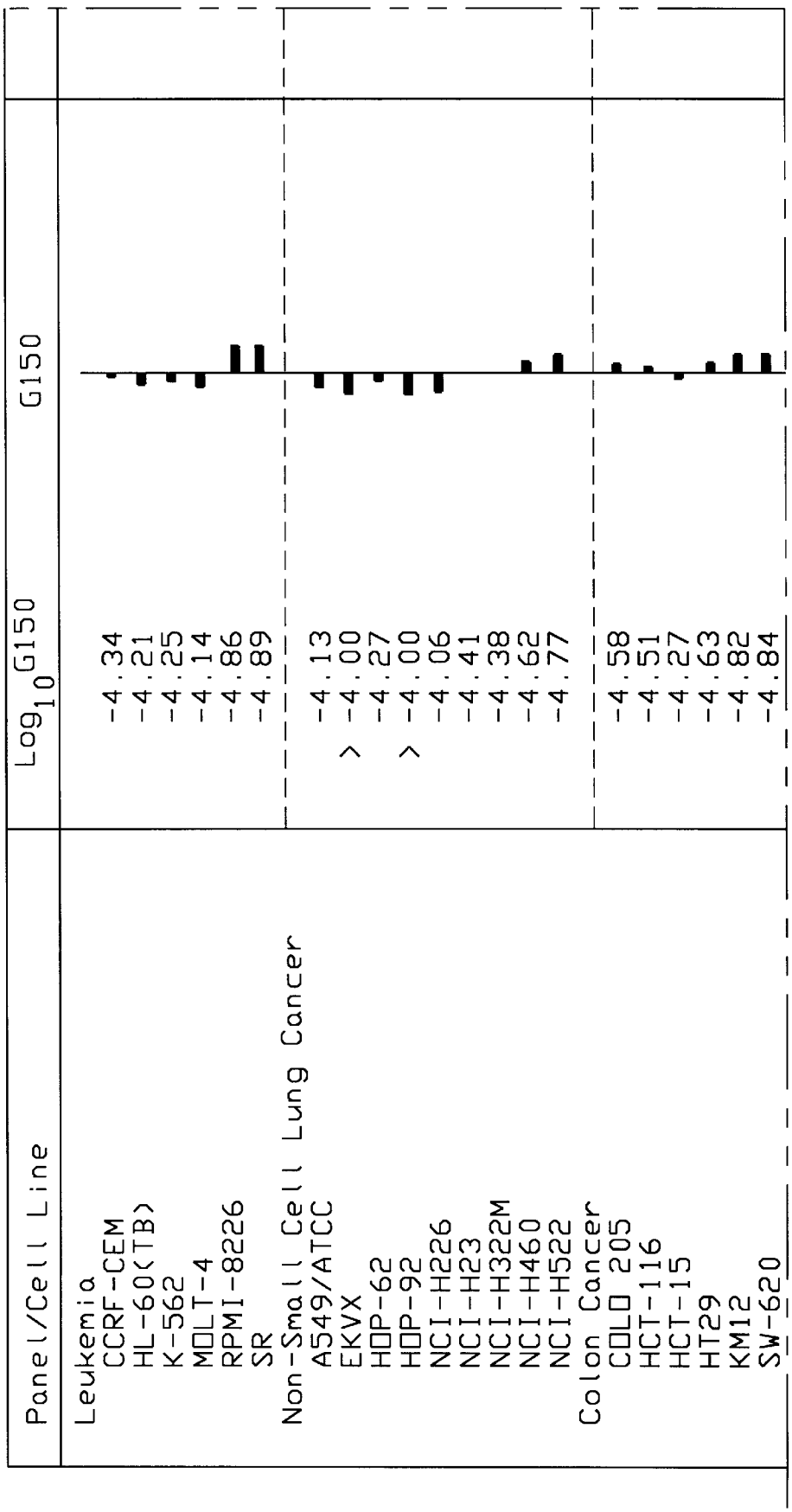
FIG. 19 represent mean graphs of dose response of baccatin III in a screen of sixty tumor cell lines.
Figure 19C:
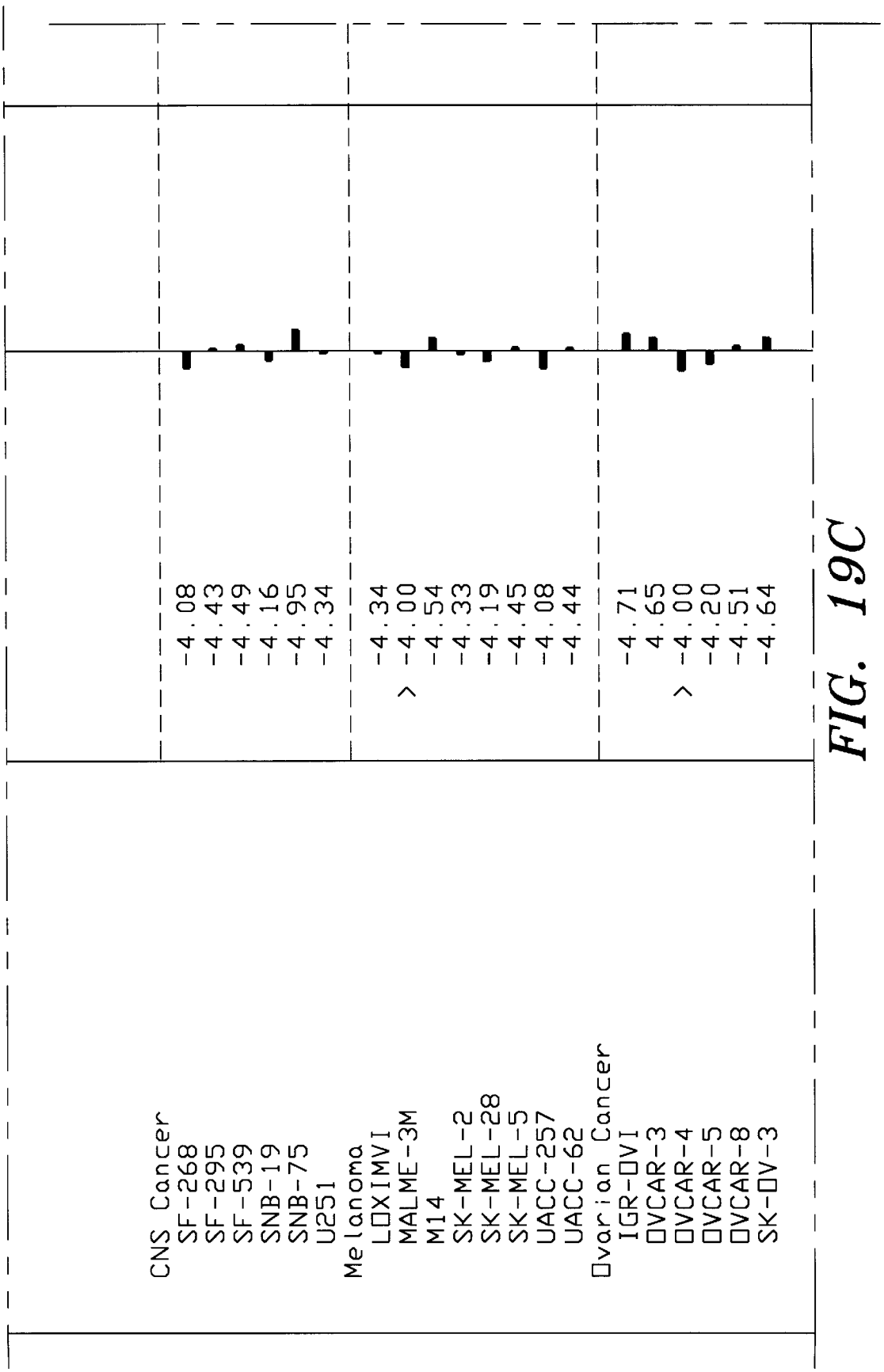
Figure 19D:
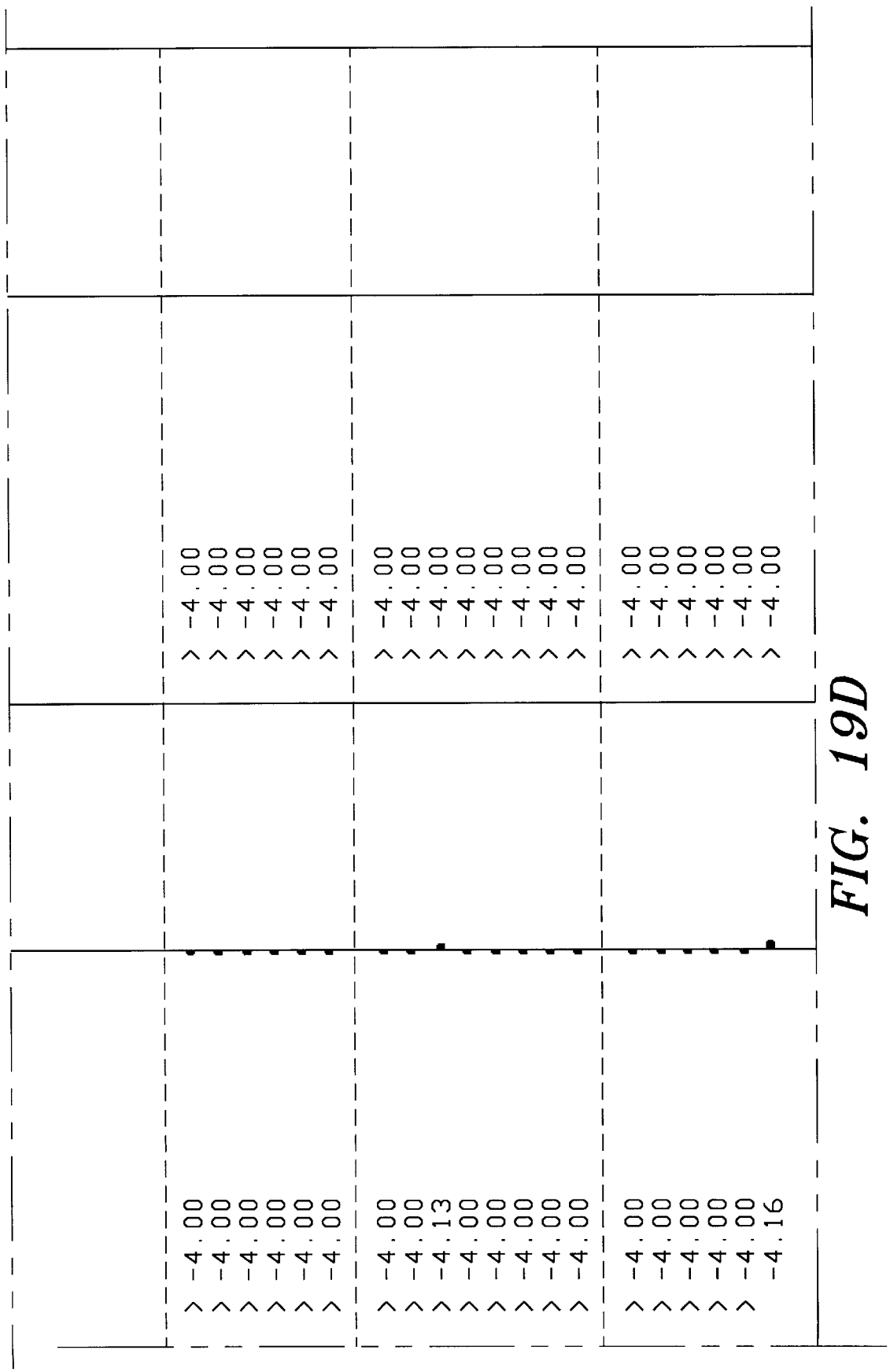
Figure 19E:
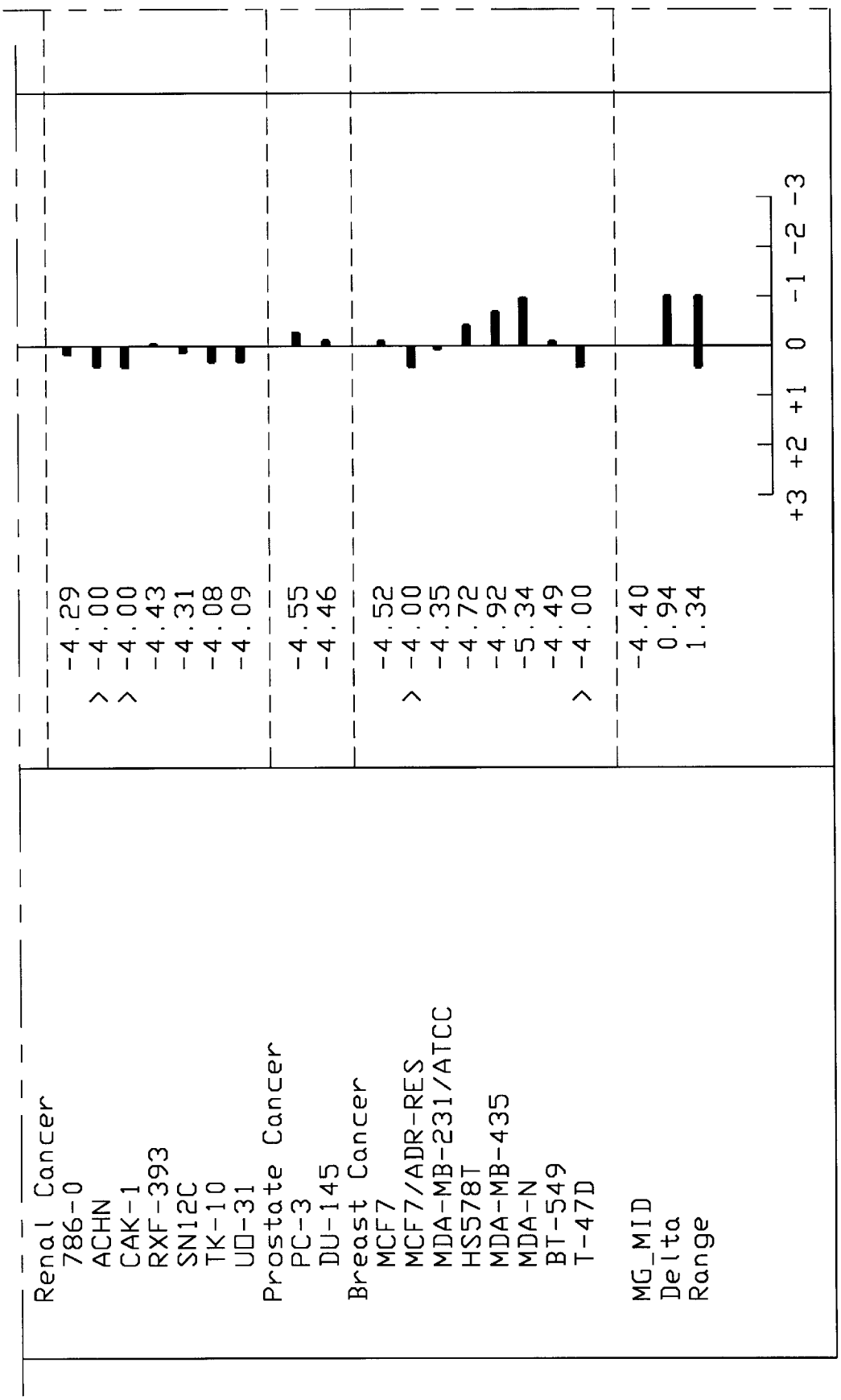
Figure 19F:
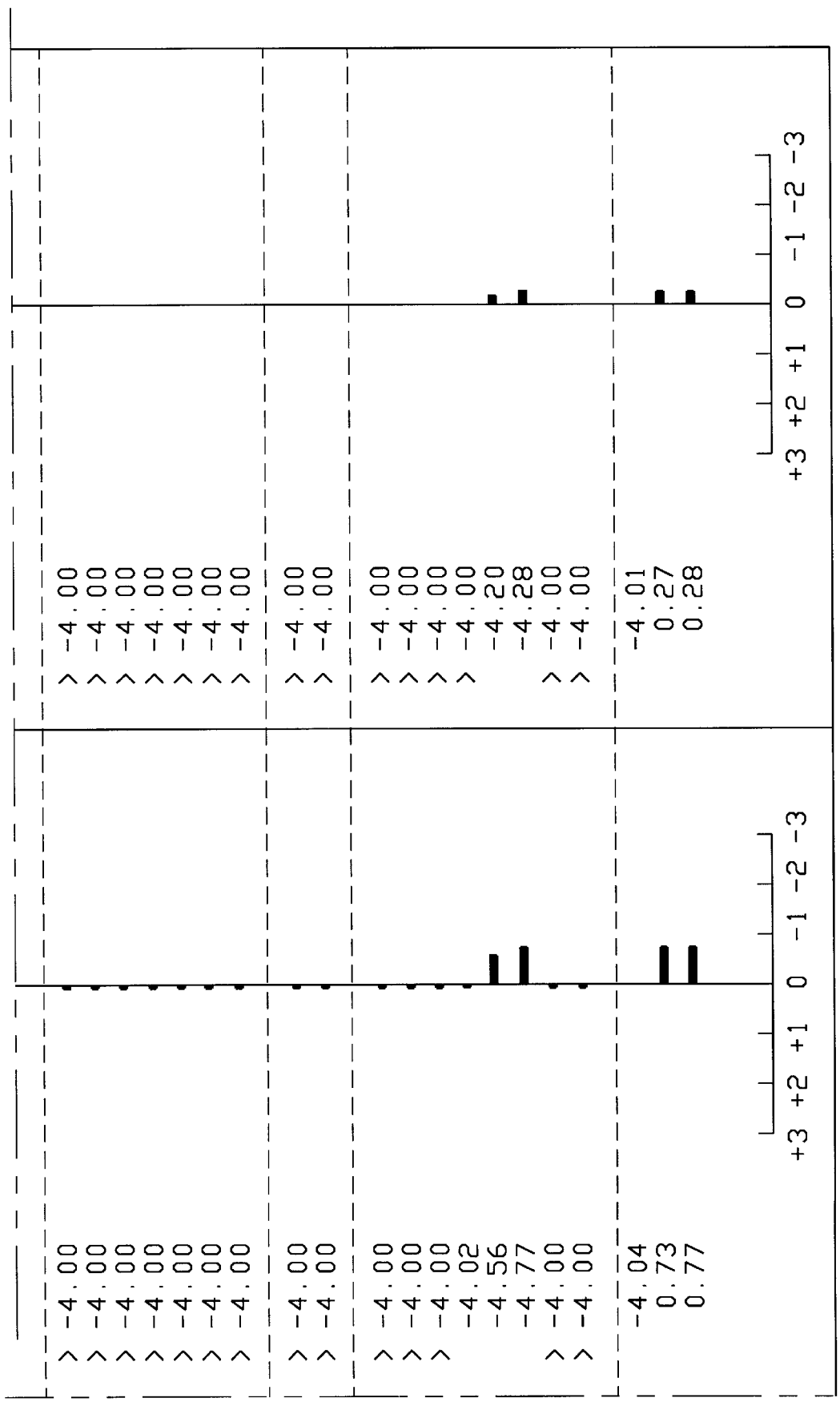

Operation and interpretation of the screen are discussed in detail in Boyd et al., as well as in several other articles cited therein and thus need not be repeated here, except comparative results obtained from the screen between the novel 2"3"-dibromocephalomannine compound represented as compound "XC-LY-40-175-9 analog" and that of the known antitumor compounds, paclitaxel, taxotere and baccatin III. In vitro antitumor efficacy of dibromocephalomannine is shown in FIGS. 15 and 16, Testing Results and Mean Graphs, respectively.

In corresponding manner, in vitro antitumor efficacy is shown in FIGS. 17–19 by dose response represented by mean graphs of paclitaxel, taxotere and baccatin III, respectively.

Discussion of Results

In the NCI in vitro anticancer drug screen, the effect of an antitumor candidate, i.e. 2", 3"-dibromocephalomannine of the present invention, on a cell line, percentage growth (PG), and calculated response parameters are discussed in detail in Boyd et al., *Data display and analysis strategies for the NCI—disease— oriented in vitro antitumor drug Screen*, Cytotoxic Anticancer Drugs: Models and Concepts for Drug Discovery and Development, Kluwer Academic Publishers, Amsterdam, pp. 11–34 (1992), and Monks et al. *Feasibility of a high-flux anticancer drug screen utilizing a diverse panel of human tumor cell lines in culture*, J. Natl. Cancer Inst. 83:757–766 (1991), the entire disclosures of which are incorporated herein by reference. In general, in the screening data report, FIG. 15, and mean graphs, FIGS. 16, 17, 18 and 19, "$GI_{50}$" represents the 50% growth inhibition factor, "TGI" represents a total growth inhibition, or cytostatic level of effect, and "$LC_{50}$" represents a lethal concentration, or net cell killing or cytotoxicity parameter. Values accompanied by a "<" signify that the dosage level or real value is a value that is something less than the lowest tested concentration, and values accompanied by a ">" sign indicate that the effective dosage or real value is a level greater than the highest tested concentration.

The mean graphs are obtained from $GI_{50}$, TGI and $LC_{50}$ concentrations obtained for compounds tested against each cell line in the NCI in vitro screen. A detailed discussion of mean graph construction is provided in Boyd et al. (1995). In interpreting the mean graphs in general, a bar projecting to the right represents sensitivity of a particular cell line to an anticancer candidate in excess of the average sensitivity of all tested cell lines, while bars extending to the left represent cell lines which are less sensitive on average to the anticancer candidate. As the bar scales are logarithmic, a bar which extends, for example, 2 or 3 units to the right of the vertical reference line in, say a $GI_{50}$ mean graph, indicates that the anticancer candidate achieved a response parameter for a particular cell line at a concentration one-hundredth to one-thousandth of the mean concentration required over all cell lines, therefore indicating that the particular tumor cell line is unusually sensitive to the tested candidate.

Turning now to FIG. 16, the inventive 2",3"-dibromocephalomannine of this invention shows a relative high magnitude of effect in TGI, for example, on Leukemia cell line HL-60(TB); Non-Small Cell Lung Cancer line NCI-H522; Colon Cancer cell lines COLO 205 and HT 29; CNS Cancer cell lines SF-539 and SNB-75; Ovarian Cancer Cell line OVCAR-3; Renal Cancer cell line RXF-393; and Breast Cancer cell lines MCF7, MDA-MB-231/ATCC, HS 578T, MDA-MB-435 and MDA-N.

In comparison with FIG. 17, analysis of the well known antitumor compound paclitaxel, the inventive dibromocephalomannine compound demonstrates an unusually high magnitude of response such as that of paclitaxel to Non-Small Cell Lung Cancer cell line NCI-H522 (←−8 v. ←−10 for dibromocephalomannine and paclitaxel, respectively). Compare also the respectively high magnitude of response of both dibromocephalomannine and paclitaxel on Colon Cancer Cell line COLO 205 (←−8 v. −7.97); on CNS cancer cell line SNB-75 (−7.30 v. −9.18), and, for example, on Breast Caner Cell line HS 5787 (−7.61 v. −9.91).

The high magnitude of effect of dibromocephalomannine on many cell lines is perhaps more pronounced in $GI_{50}$ in which dibromocephalomannine demonstrates a high response level in many of the same cell lines as does paclitaxel, such as, for example, with various tested colon cancer cell lines, melonoma cell lines, ovarian cancer cell lines, and renal cancer cell lines, and falls within the footprint of paclitaxel-like antitumor activity thereby reproducibly demonstrating the high antitumor efficacy of the novel 2", 3"-dibromocephalomannine compound.

We claim:

1. 2",3"-dihalocephalomannine of the formula 1:

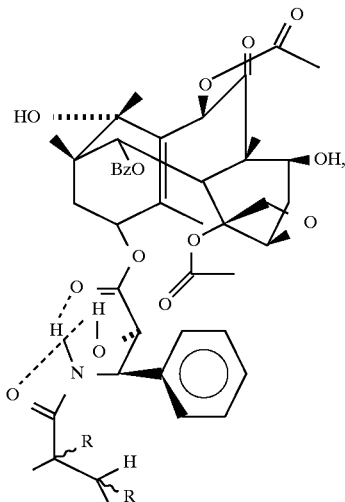

wherein R is halogen.

2. The compound of formula 1, wherein R is bromine.

3. A pharmaceutical formulation which comprises as an active ingredient of the compound of claims 1 or 2, or a pharmaceutically acceptable salt thereof, associated with one or more pharmaceutically acceptable carriers, excipients or diluents therefor.

4. A method of treating a patient's tumor in need of treatment which comprises administering to said patient a tumor sensitive amount of the compounds of claims 1 or 2.

* * * * *